(12) United States Patent
Pan et al.

(10) Patent No.: US 8,912,137 B2
(45) Date of Patent: *Dec. 16, 2014

(54) METHOD FOR INCREASING NATRIURESIS OR DIURESIS BY ISOFORMS OF BRAIN NATRIURETIC PEPTIDE

(75) Inventors: Shuchong Pan, Rochester, MN (US); Robert D. Simari, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 117 days.

This patent is subject to a terminal disclaimer.

(21) Appl. No.: 13/616,244

(22) Filed: Sep. 14, 2012

(65) Prior Publication Data

US 2013/0143816 A1    Jun. 6, 2013

Related U.S. Application Data

(63) Continuation of application No. 10/561,014, filed as application No. PCT/US2004/017554 on Jun. 2, 2004, now Pat. No. 8,354,496.

(60) Provisional application No. 60/480,460, filed on Jun. 20, 2003.

(51) Int. Cl.
| | | |
|---|---|---|
| A61K 38/00 | (2006.01) | |
| A61K 38/22 | (2006.01) | |
| A61K 47/00 | (2006.01) | |
| C07K 14/575 | (2006.01) | |
| C07K 14/58 | (2006.01) | |
| A61P 13/12 | (2006.01) | |
| A61P 9/00 | (2006.01) | |

(52) U.S. Cl.
CPC .................................. C07K 14/575 (2013.01)
USPC ............. 514/1.1; 514/1.3; 514/12.4; 514/9.7; 514/15.4; 514/15.6

(58) Field of Classification Search
None
See application file for complete search history.

(56) References Cited

U.S. PATENT DOCUMENTS

| | | | |
|---|---|---|---|
| 4,034,074 | A | 7/1977 | Miles |
| 4,098,876 | A | 7/1978 | Piasio et al. |
| 4,233,402 | A | 11/1980 | Maggio et al. |
| 4,496,544 | A | 1/1985 | Needleman |
| 4,996,143 | A | 2/1991 | Heller et al. |
| 5,114,923 | A | 5/1992 | Seilhamer et al. |
| 5,212,286 | A | 5/1993 | Lewicki et al. |
| 5,296,347 | A | 3/1994 | LaMotte, III |
| 5,434,133 | A | 7/1995 | Tanaka et al. |
| 5,565,322 | A | 10/1996 | Heller |
| 5,580,859 | A | 12/1996 | Felgner et al. |
| 5,583,108 | A | 12/1996 | Wei et al. |
| 5,589,466 | A | 12/1996 | Felgner et al. |
| 5,665,704 | A | 9/1997 | Lowe et al. |
| 5,674,710 | A | 10/1997 | Seilhamer |
| 5,846,932 | A | 12/1998 | Lowe et al. |
| 5,849,489 | A | 12/1998 | Heller |
| 5,948,761 | A | 9/1999 | Seilhamer et al. |
| 6,124,430 | A | 9/2000 | Mischak et al. |
| 6,162,603 | A | 12/2000 | Heller |
| 6,376,207 | B1 | 4/2002 | Mischak et al. |
| 6,551,795 | B1 | 4/2003 | Rubenfield et al. |
| 6,586,396 | B1 | 7/2003 | Seilhamer et al. |
| 6,812,339 | B1 | 11/2004 | Venter et al. |
| 6,818,619 | B2 | 11/2004 | Burnett, Jr. et al. |
| 6,828,107 | B2 | 12/2004 | Asada et al. |
| 6,849,714 | B1 | 2/2005 | Bridon et al. |
| 6,887,470 | B1 | 5/2005 | Bridon et al. |
| 6,887,481 | B1 | 5/2005 | Chan et al. |
| 6,897,030 | B2 | 5/2005 | Seilhamer et al. |
| 6,974,861 | B2 | 12/2005 | Seilhamer et al. |
| 7,179,790 | B2 | 2/2007 | Seilhamer |
| 7,214,786 | B2 | 5/2007 | Kovalic et al. |
| 7,332,569 | B2 | 2/2008 | Cojocaru et al. |
| 8,324,162 | B2 | 12/2012 | Simari et al. |
| 8,354,496 | B2 | 1/2013 | Pan et al. |
| 8,357,656 | B2 | 1/2013 | Simari et al. |
| 2004/0123343 | A1 | 6/2004 | La Rosa et al. |
| 2007/0281887 | A1 | 12/2007 | Pan |
| 2013/0143820 | A1 | 6/2013 | Simari et al. |

FOREIGN PATENT DOCUMENTS

| | | |
|---|---|---|
| WO | WO 84/03285 | 8/1984 |
| WO | WO 84/03825 | 10/1984 |
| WO | WO 95/24419 | 9/1995 |
| WO | WO 00/71576 | 11/2000 |
| WO | WO 01/44284 | 6/2001 |
| WO | WO 02/24895 | 3/2002 |
| WO | WO 2005/000095 | 1/2005 |
| WO | WO 2005/072055 | 8/2005 |

OTHER PUBLICATIONS

Office action from Chinese Application No. 200480020964.7 mailed Mar. 2, 2011, 6 pages.
European Search Report for European Application No. 04754213 mailed Sep. 5, 2008, 6 pages.
Office action from European Application No. 10187879.1 dated Nov. 27, 2013, 7 pages.
Office action in Japanese Application No. 2006-517173, mailed Jul 26, 2011, 3 pages.
Office action in Chinese Application No. 200780029445.0, mailed Apr. 19, 2011, 10 pages.
Office action in Chinese Application No. 200780029445.0, mailed Mar. 7, 2012, 8 pages.
Office action in European Application No. 07813886.4 dated Apr. 16, 2010, 1 page.

(Continued)

*Primary Examiner* — Chang-Yu Wang
(74) *Attorney, Agent, or Firm* — Fish & Richardson P.C.

(57) ABSTRACT

Methods and materials for diagnosing and treating heart conditions (e.g., heart failure) and kidney conditions (e.g., kidney failure) are described.

5 Claims, 4 Drawing Sheets

(56) References Cited

OTHER PUBLICATIONS

Office action in European Application No. 07813886.4 dated Oct. 11, 2011, 6 pages.
Office action from European Application No. 07813886.4, dated Sep. 26, 2013, 5 pages.
Office action in Israeli Application No. 196931, dated Mar. 3, 2011, 3 pages.
Office action from Israeli Application No. 196931, dated Apr. 12, 2013, 2 pages.
Office action from Japanese Application No. 2009-523978, mailed Jul. 31, 2013, 6 pages.
Supplementary European Search Report and Annex in European Application No. 07 81 3886, Completed Jan. 26, 2010, 7 pages.
International Search Report and Written Opinion in International Application No. PCT/US2004/017554, mailed Oct. 18, 2007, 12 pages.
International Preliminary Report on Patentability in International Application No. PCT/US2004/017554, mailed Nov. 15, 2007, 6 pages.
Authorized Officer A. Nickitas-Etienne. International Preliminary Report on Patentability in International Application No. PCT/US2008/076434, issued Mar. 16, 2010, 6 pages.
Authorized Officer H. K. Cho. International Search Report and Written Opinion of the International Searching Authority in International Application No. PCT/US2008/076434, mailed May 19, 2009, 8 pages.
Authorized Officer S. Baharlou. International Preliminary Reprt on Patentability in International Application No. PCT/US2007/075465, mailed Feb. 19, 2009, 8 pages.
Authorized Officer W. H. Shin. International Search Report in International Application No. PCT/US2007/075465,mailed Dec. 18, 2007, 15 pages.
Extended European search report from European Application No. 10187879.1, dated Mar. 9, 2011, 7 pages.
Office action from Chinese Application No. 200480020964.7, dated Aug. 9, 2010, 16 pages.
Office action from European Application No. 04754213.9, dated Jan. 20, 2009, 7 pages.
Office action from European Application No. 04754213.9, dated May 29, 2009, 6 pages.
Office action from Israel Application No. 172674, dated Apr. 5, 2009, 2 pages.
Office action from Israel Application No. 172674, dated Aug. 8, 2010, 2 pages.
Office action from Japanese Application No. 2006-517173, dated Feb. 16, 2010, 6 pages.
Japanese Office Action in Japanese Application No. 2009-523978, dated Jul. 25, 2012, 15 pages.
Non-Final Office Action in U.S. Appl. No. 10/561,014, mailed Sep. 5, 2008, 23 pages.
Final Office Action in U.S. Appl. No. 10/561,014, mailed Jun. 12, 2009, 18 pages.
Non-Final Office Action in U.S. Appl. No. 10/561,014, mailed Dec. 29, 2009, 13 pages.
Final Office Action in U.S. Appl. No. 10/561,014, mailed Jul. 21, 2010, 11 pages.
Non-Final Office Action in U.S. Appl. No. 10/561,014, mailed Oct. 12, 2011, 14 pages.
Non-Final Office Action in U.S. Appl. No. 12/376,880, mailed Feb. 27, 2012, 16 pages.
Non-Final Office Action in U.S. Appl. No. 12/677,838, mailed Apr. 19, 2012, 9 pages.
Abbey and Potter, "Vasopressin-dependent inhibition of the C-type natriuretic peptide receptor, NPR-B/GC-B, requires elevated intracellular calcium concentrations," *J. Biol. Chem.*, 2002, 277:42423-42430.
Abdelhafiz, "Heart failure in older people: causes, diagnosis and treatment," *Age Ageing*, 2002, 31(1):29-36.
Anand-Srivastava, "Natriuretic peptide receptor-C signaling and regulation," *Peptides*, 2005, 26:1044-1059.

Ausubel et al. (eds.), *Short Protocols in Molecular Biology*, 1992, Chapters 8 and 11, Green Publishing Associates and John Wiley & Sons.
Best et al., "Dendroaspis natriuretic peptide relaxes isolated human arteries and veins," *Cardiovas. Res.*, 2002, 55:375-384.
Bowie et al., "Deciphering the Message in Protein Sequences: Tolerance to Amino Acid Substitutions," *Science*, 1990, 247:1306-1310.
Bryan and Potter, "The atrial natriuretic peptide receptor (NPR-A/GC-A) is dephosphorylated by distinct microcystin-sensitive and magnesium-dependent protein phosphates," *J. Biol. Chem.*, 2002, 277:16041-16047.
Burger and Burger, BNP in decompensated heart failure: heart failure: Diagnostic, prognostic and therapeutic potential, *Curr. Opin. Investig. Drugs*, 2001, 2(7):929-35.
Burgess et al., "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue," *J of Cell Biol.*, 1990, 111:2129-2138.
Chaurand et al., "Peptide and Protein Identification by Matrix-Assisted Laser Desorption Ionization (MALDI) and MALDI-Post-Source Decay Time-of-Flight Mass Spectrometry," *J. Am. Soc. Mass Spectrom.*, 1999, 10(2):91-103.
Chen et al. "A novel designer natriuretic and diuretic peptide based upon an alternatively spliced BNP without vascular vasodilatory actions," *Circulation*, 2006, 114(18):270 (Abstract 1412).
Chen et al., "Equimolar doses of atrial and brain natriuretic peptides and urodilatin have differential renal actions in overt experimental heart failure," *Am. J. Physiol. Regul. Integr. Comp. Physiol.*, 2005, 288:R1093-R1097.
Chen et al., "Renal response to acute neutral endopeptidase inhibition in mild and severe experimental heart failure," *Circulation*, 1999, 100:2443-2448.
Cole et al., "The EBV-Hybridoma Technique and Its Application to Human Lung Cancer," *Monoclonal Antibodies and Cancer Therapy*, 1985, Alan R. Liss, Inc., pp. 77-96.
Costello-Boerrigter et al., "Vasopressin-2-receptor antagonism augments water excretion without changes in renal hemodynamics or sodium and potassium excretion in human heart failure," *Am. J. Physiol. Renal Physiol.*, 2006, 290:F273-F278.
Cote et al., "Generation of human monoclonal antibodies reactive with cellular antigens," *Proc. Natl. Acad. Sci. USA*, 1983, 80:2026-2030.
Cowie and Mendez, "BNP and congestive heart failure," *Prog. Cardiovasc. Dis.*, 2002, 44(4):293-321.
Fan et al., "Down-regulation does not mediate natriuretic peptide-dependent desensitization of natriuretic peptide receptor (NPR)-A or NPR-B: guanylyl cyclase-linked natriuretic peptide receptors do not internalize," *Mol. Pharmacol.*, 2005, 67:174-183.
Genbank Accession No. ADW08083, dated Jan. 30, 2011, 1 page.
Genbank Accession No. AEB63460, dated Jun. 17, 2011, 1 page.
GenBank Accession No. BQ130005 dated Jul. 15, 2003.
GenBank Accession No. BQ130258 dated Jul. 15, 2003.
GenBank Accession No. M25296 dated Apr. 27, 1993.
Gevaert et al., "Protein identification based on matrix assisted laser desorption/ionization-post source decay-mass spectrometry," *Electrophoresis*, 2001, 22(9):1645-51.
Guatelli et al., "Isothermal, in vitro amplification of nucleic acids by a multienzyme reaction modeled after retroviral replication," *Proc. Natl. Acad. Sci. USA*, 1990, 87:1874-1878.
Haber et al., "Application of a radioimmunoassay for angiotensin I to the physiologic measurements of plasma renin activity in normal human subjects," *J. Clin. Endocrinol.*, 1969, 29:1349-1355.
Huse et al., "Generation of a Large Combinatorial Library of the Immunoglobulin Repertoire in Phage Lambda," *Science*, 1989, 246:1275-1281.
Hyrup and Nielsen, "Peptide Nucleic Acids (PNA): Synthesis, Properties and Potential Applications," *Bioorgan. Med. Chem.*, 1996, 4:5-23.
Köhler and Milstein, "Continuous cultures of fused cells secreting antibody of predefined specificity," *Nature*, 1975, 256:495-497.
Kozbor and Roder, "The production of monoclonal antibodies from human lymphocytes," *Immunology Today*, 1983, 4:72-79.

(56) References Cited

OTHER PUBLICATIONS

Lewis, "PCR's Competitors Are Alive and Well and Moving Rapidly Towards Commercialization," *Genetic Engineering News*, 1992, 12(9):1-3.

Margulies et al., "Induction and prevention of radiocontrast-induced nephropathy in dogs with heart failure," *Kidney International*, 1990, 38(6):1101-1108.

Mathur et al., "Nesiritide—A new agent for acute decompensated heart failure," *MJAFI*, 2005, 61(4):375-376.

McCurley et al., "Furosemide and the progression of left ventricular dysfunction in experimental heart failure," *J. Am. Coll. Cardiol.*, 2004, 44(6):1301-1307.

Ogawa et al., "Molecular cloning of the complementary DNA and gene that encode mouse brain natriuretic peptide and generation of transgenic mice that overexpress the brain natriuretic peptide gene," *J. Clin. Invest.*, 1994, 93(5):1911-1921.

Pan et al., "Biodesign of a renal-protective peptide based on alternative splicing of B-type natriuretic peptide," *Proc. Natl. Acad. Sci. USA*, 2009, 106(27):11282-11287.

Pawson and Nash, "Assembly of Cell Regulatory Systems through Protein Interaction Domains," *Science*, 2003, 300:445-452.

Peacock, "The B-type natriuretic peptide assay: a rapid test for heart failure," *Cleve. Clin. J. Med.*, 2002, 69(3):243-251.

Richards et al., "BNP in hormone-guided treatment of heart failure," *Trends Endocrinol. Metab.*, 2002, (5):151-155.

Rose et al., "C-type natriuretic peptide activates a non-selective cation current in acutely isolated rat cardiac fibroblasts via natriuretic peptide C receptor-mediated signaling," *J. Physiol.*, 2007, 580(Pt. 1):255-274.

Sabbatini et al., "Atrial natriuretic factor stimulates exocrine pancreatic secretion in the rat through NPR-C receptors," *Am. J. Physiol. Gastrointest. Liver Physiol.*, 2003, G929-G937.

Sabbatini et al., "C-type natriuretic peptide stimulates pancreatic exocrine secretion in the rat: Role of vegal afferent and efferent pathways," *Eur. J. Pharmacol.*, 2007, 577:192-202.

Sackner-Bernstein et al., Risk of worsening renal function with nesiritide in patients with acutely decompensated heart failure, *Circulation*, 2005, 111:1487-1491.

Sagnella, "Practical implications of current natriuretic peptide research," *J. Renin. Angiotensin Aldosterone Syst.*, 2000, 1(4):304-315.

Summerton and Weller, "Morpholino Antisense Oligomers: Design, Preparation, and Properties," *Antisense Nucleic Acid Drug Dev.*, 1997, 7:187-195.

Suzuki et al., "The role of the natriuretic peptides in the cardiovascular system," *Cardiovascular Res.*, 2001, 51:489-494.

Tremblay et al., "Biochemistry and physiology of the natruiretic peptide receptor guanylyl cyclases," *Mol. Cell. Biochem.*, 2002, 230(1-2):31-47.

Valli et al., "Review of 10 years of the clinical use of brain natriuretic peptide in cardiology," *J. Lab. Clin. Med.*, 1999, 134(5):437-444.

Walther et al., "Natriuretic peptide system in fetal heart and circulation," *J. Hypertens.*, 2002, 20(5):786-791.

Wei et al., "Atrial and pulmonary endothelin mRNA is increased in a canine model of chronic low cardiac output," *Am. J. Physiol.*, 1997, 273:R838-844.

Weiss, "Hot Prospect for New Gene Amplifier," *Science*, 1991, 254:1292-1293.

Pan et al., "Alternatively spliced forms of human BNP: Discovery, localization, and function" Circulation, vol. 110, No. 17, Suppl. III, p. III-96, Abstract 452, Oct. 26, 2004.

Office action for Canadian Application No. 2660294 dated May 8, 2014, 3 pages.

Office action from Japanese Application No. 2009/523978 mailed May 22, 2014, 6 pages.

Human BNP2:

Nucleotide sequence:
atggatccccagacagcaccttcccggggcgctcctgctcctgctcttcttgcatctggctttcctgggaggtcgttccca
cccgctgggcagccccggttcagcctcggacttggaaacgtccgggttacaggagcagcgcaaccatttgcagggcaaac
tgtcggagctgcaggtggagcagacatccctggagcccctccaggagagcccccgtcccacaggtgtctggaagtcccgg
gaggtagccaccgagggcatccgtgggcaccgcaaaatggtcctctacaccctgcgggcaccacgaagcccaagatggt
gcaagggtctggctgctttgggaggaagatggaccggatcagctcctccagtggcctgggctgcaaaggtaagcacccccc
tgccaccccggccgccttcccccattccagtgtgtgacactgttagagtcactttggggtttgttgtctctgggaaccac
actctttga (SEQ ID NO:5)

Amino acid sequence:
MDPQTAPSRALLLLLFLHLAFLGGRSHPLGSPGSASDLETSGLQEQRNHLQGKLSE
LQVEQTSLEPLQESPRPTGVWKSREVATEGIRGHRKMVLYTLRAPR<u>SPKMVQGSG
CFGRKMDRISSSSGLGCKGKHPLPPRPPSPIPVCDTVRVTLGFVVSGNHTL</u> (SEQ
ID NO:3)

GKHPLPPRPPSPIPVCDTVRVTLGFVVSGNHTL (SEQ ID NO:1)

B.

DOG BNP-2

Nucleotide sequence:
atggagccctgcgcagcgctgccccgggcccctcctgctcctcctgttcttgcacctgtcgccactcggaggccgccccca
cccgctgggcggccgcagccccacctcggaagcctcggaagcctcggaagcctcggggttgtgggccgtgcaggagctgc
tgggccgtctgaaggacgcagttcagagctgcaggcagagcagttggccctggaaccctgcaccggagccacagcccc
gcagaagccccggaggccggggaggaacgccccgtgggggtccttgcacccccatgacagtgtcctccaggccctgagaag
actacgcagccccaagatgatgcacaagtcagggtgctttggccggaggctggaccggatcggctccctcagtggcctgg
gctgcaatggtaagccgcctccctgccaccttggctcccctccccagccccctgggttcgacccttggaacccttctg
ggtttgttgtctcggggggatcacactctga (SEQ ID NO:38)

Amino acid sequence:
MEPCAALPRALLLLLFLHLSPLGGRPHPLGGRSPTSEASEASEASGLWAVQELLGR
LKDAVSELQAEQLALEPLHRSHSPAEAPEAGEERPVGVLAPHDSVLQALRRL<u>RSP
KMMHKSGCFGRRLDRIGSLSGLGCNGKPPPCHLGSPSPAPWVRPLEPLLGLLSRGI
TL</u> (SEQ ID NO:14)

FIG. 2

Human BNP-3

Nucleotide sequence:
atggatccccagacagcaccttcccggggcgctcctgctcctgctcttcttgcatctggctttcctggggaggtcgttccca
cccgctgggcagccccggttcagcctcggacttggaaacgtccgggttacaggagcagcgcaaccatttgcagggcaaac
tgtcggagctgcaggtggagcagacatccctggagcccctccaggagagcccccgtcccacaggtgtctggaagtcccgg
gaggtagccaccgagggcatccgtgggcaccgcaaaatggtcctctacaccctgcgggcaccacgaagccccaagatggt
gcaagggtctggctgctttgggaggaagatggaccggatcagctcctccagtggcctgggctgcaaagtggtgcagaaag
agaaccaaacatttcctcctggtttcctctaa (SEQ ID NO:6)

Amino acid sequence:
MDPQTAPSRALLLLLFLHLAFLGGRSHPLGSPGSASDLETSGLQEQRNHLQGKLSE
LQVEQTSLEPLQESPRPTGVWKSREVATEGIRGHRKMVLYTLRAPR<u>SPKMVQGSG
CFGRKMDRISSSSGLGCKVVQKENQTFPPGFL</u> (SEQ ID NO:4)

VVQKENQTFPPGFL (SEQ ID NO:2)

FIG. 4

BNP

SPKMVQGSGCFGRKMDRISSSSGLGCKVLRRH (SEQ ID NO:16)

DNP

EVKYDPCFGHKIDRINHVSNLGCPSLRDPRPNAPSTSADNP (SEQ ID NO:17)

ANP

SLRRSSCFGGRMDRIGAQSGLGCNSFRY (SEQ ID NO:18)

CNP

GLSKGCFGLKLDRIGSMSGLGC (SEQ ID NO:19)

METHOD FOR INCREASING NATRIURESIS OR DIURESIS BY ISOFORMS OF BRAIN NATRIURETIC PEPTIDE

CROSS-REFERENCE TO RELATED APPLICATION

This application is a continuation of U.S. application Ser. No. 10/561,014, filed Jun. 6, 2006, now U.S. Pat. No. 8,354, 496, which is a National Stage application under 35 U.S.C. §371 of International Application No. PCT/US2004/017554, having an International Filing Date of Jun. 2, 2004, which claims benefit of priority from U.S. Provisional Patent Application No. 60/480,460, filed Jun. 20, 2003.

TECHNICAL HELD

The invention relates to methods and materials for diagnosing heart conditions such as heart failure, and more particularly, for diagnosing heart conditions by detecting isoforms of brain natriuretic peptide (BNP). The invention also relates to methods and materials for treating heart conditions (e.g., heart failure) and kidney conditions (e.g., kidney failure).

BACKGROUND

Members of the natriuretic peptide family are hormones that regulate body fluid homeostasis. Atrial natriuretic peptide (ANP) is secreted by atrial myocytes in response to increased intravascular volume. Once ANP is in the circulation, its effects are primarily on the kidney, vascular tissue, and adrenal gland, in which its actions lead to the excretion of sodium and water by the kidneys and a decrease in intravascular volume and blood pressure. BNP also is of myocardial cell origin, and like ANP, it circulates in human plasma. BNP is natriuretic, rennin inhibiting, vasodilating, and lusitropic. The main circulating and storage form of BNP is a 32 amino acid peptide with a ring structure. Physiological actions of BNP are mediated through a guanylate cyclase-linked receptor, natriuretic peptide receptor A (NPR-A). Clearance of BNP is promoted by a NPR-C receptor that removes it from the circulation. BNP also is degraded through enzymatic cleavage by neutral endopeptidase. C-type natriuretic peptide (CNP) is of endothelial cell origin and functions as a vasodilating and growth-inhibiting peptide. *Dendroaspis* natriuretic peptide (DNP) is similar in structure to ANP, BNP, and CNP, and is isolated from the venom of *Dendroaspis angusticeps* or green mamba snake.

ANP and BNP are increased in the plasma and heart during congestive heart failure in humans, and exert cardiorenal protective actions in addition to serving as serum markers for ventricular dysfunction. Epidemiological evidence indicates that at least 3% of the adult population above the age of 45 may have ventricular systolic dysfunction and 52% may be asymptomatic.

SUMMARY

The invention is based on the identification of novel forms of BNP generated by alternative splicing. Alternatively spliced human BNP isoforms contain the 17-amino-acid disulfide ring structure of BNP, have unique carboxy-termini, and result from distinct splicing variation. One of the isoforms, BNP2, has a unique 33 amino acid residue C-terminal extension attached to the ring. This isoform is the result of intron 2 inclusion. BNP3 contains a novel 14 amino acid residue C-terminal extension and is the result of an alternative splice acceptor present within intron 2. As described herein, expression of BNP2 and BNP3 is increased in cardiomyocytes during heart failure. Thus, BNP2 and BNP3 polypeptides or ribonucleic acids encoding BNP2 or BNP3 can be used as markers for heart conditions. As such, the presence, absence, or level of such polypeptides or ribonucleic acids can be used to diagnose heart conditions and monitor treatment of heart conditions. In addition, BNP2 and BNP3 can be used as therapeutics for the treatment of heart conditions.

The invention features a purified polypeptide and an antibody having specific binding affinity for the polypeptide. The polypeptide includes an amino acid sequence selected from the group consisting of the amino acid sequence of SEQ ID NO:1, 2, 3, 4, 35, or 36; a sequence having at least 6 contiguous residues of the amino acid sequence of SEQ ID NO:1 or SEQ ID NO:2; a sequence having at least 65% sequence identity to the amino acid sequence of SEQ ID NO:1 SEQ ID NO:2; and a sequence having at least 65% sequence identity to a fragment of SEQ ID NO:1 or SEQ ID NO:2 at least six contiguous residues in length. The amino acid sequence can have at least 75% (e.g., 80, 90, or 95%) sequence identity to the amino acid sequence of SEQ ID NO:1 or SEQ ID NO:2 or at least 75% (e.g., 80, 90, or 95%) sequence identity to a fragment of SEQ ID NO:1 or SEQ ID NO:2 at least 6 contiguous residues in length. In some embodiments, the polypeptide can include the amino acid sequence of SEQ ID NO:35 or SEQ ID NO:36. Pharmaceutical compositions can include a polypeptide and a pharmaceutically acceptable carrier.

In another aspect, the invention features an isolated nucleic acid encoding a purified polypeptide described above, vectors that include the nucleic acids, and host cells that include the vectors. The polypeptide can be encoded by the nucleic acid sequence of SEQ ID NO:5; the nucleic acid sequence of nucleotides 383 to 489 of SEQ ID NO:5; the nucleic acid sequence of SEQ ID NO:6; or the nucleic acid sequence of nucleotides 388 to 432 of SEQ ID NO:6. The host cells can be eukaryotic host cells.

The invention also features a chimeric natriuretic polypeptide. The polypeptide includes a first region and a second region, the first region having an amino acid sequence selected from the group consisting of a) the sequence of residues 1 to 27 of SEQ ID NO:16; b) the sequence of residues 1 to 25 of SEQ ID NO:17; c) the sequence of residues 1 to 23 of SEQ ID NO:18; d) the sequence of residues 1 to 22 of SEQ ID NO:19; and e) the sequence of a), b), c), or d) with one to five amino acid substitutions; and the second region having an amino acid sequence selected from the group consisting of: f) the sequence of SEQ ID NO:1 or SEQ ID NO:2; g) a sequence having at least 6 contiguous residues of the amino acid sequence of SEQ ID NO:1 or SEQ ID NO:2; h) a sequence having at least 65% sequence identity to the amino acid sequence of SEQ ID NO:1 or SEQ ID NO:2; and i) a sequence having at least 65% sequence identity to a fragment of SEQ ID NO:1 or SEQ ID NO:2 at least six contiguous residues in length.

In another aspect, the invention features a purified polypeptide that includes an amino acid sequence of the formula: Gly-$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-$Xaa_{18}$-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$Xaa_{27}$-$Xaa_{28}$-$Xaa_{29}$-$Xaa_{30}$-$Xaa_{31}$-$Xaa_{32}$ (SEQ ID NO:20), wherein $Xaa_1$ is Glu or Lys; $Xaa_2$ is Pro, His, or Arg; $Xaa_3$ is Pro or Leu; $Xaa_4$ is Pro, Leu, or Ser; $Xaa_5$ is Cys or Pro; $Xaa_6$ is Pro, His, Gln, or Arg; $Xaa_7$ is Arg, Phe, or Leu; $Xaa_8$ is Asp, Gly, or absent; $Xaa_9$ is Ser, Pro, or Leu; $Xaa_{10}$ is Pro or absent; Xaa$_{11}$ is Ser, Ala, or absent; Xaa$_{12}$ is Pro or Ala; Xaa$_{13}$ is Ala, Phe, Ile, or Leu; Xaa$_{14}$ is Pro, Lys, or Leu; Xaa$_{15}$ is Val, Leu, or Trp; Xaa$_{16}$ is Cys, His, or Val; Xaa$_{17}$ is Asp, Ala, Ile, Thr, Pro, or Arg; Xaa$_{18}$ is Thr, Pro, or His; Xaa$_{19}$ is Val, Ile, Pro, Val, Ser, or Leu; Xaa$_{20}$ is Arg, Ser, Ile, or Glu; Xaa$_{21}$ is Val, Ile, Ala, or Pro; Xaa$_{22}$ is Thr, Val, or Leu; Xaa$_{23}$ is Leu, Ser, or His; Xaa$_{24}$ is Gly or Ala; Xaa$_{25}$ is Phe, Ser, Thr, or Leu; Xaa$_{26}$ is Val, Asp, or Leu; Xaa$_{27}$ is Val, Leu, or Ser; Xaa$_{28}$ is Ser, Arg, or Leu; Xaa$_{29}$ is Asn, Asp, Pro, or Thr; Xaa$_{30}$ is His, Gln, Asn, or Thr; Xaa$_{31}$ is Thr, Ile, or Ser; and Xaa$_{32}$ is Pro, Leu, Glu.

In yet another aspect, the invention features a method for diagnosing a heart condition in a patient. The method includes providing a biological sample from the patient; detecting the presence, absence, or level of BNP2 or BNP3 in the biological sample; and classifying the patient as having the heart condition or not having the heart condition based, at least in part, on the presence of BNP-2 or BNP-3, the level of BNP2 or BNP3, or the absence of BNP2 or BNP3. The heart condition can be heart failure, unstable angina, acute myocardial infarction, or hypertension. The presence, absence, or level of BNP2 can be detected or the presence, absence, or level of BNP3 can be detected. In some embodiments, the presence, absence, or level of BNP2 and BNP3 is detected.

A heart condition also can be diagnosed in a patient by providing a biological sample from the patient; detecting the presence, absence, or level of a ribonucleic acid encoding BNP2 or BNP3 in the biological sample; and classifying the patient as having the heart condition or not having the heart condition based, at least in part, on the presence of the ribonucleic acid encoding BNP2 or BNP3, the level of the ribonucleic acid encoding BNP2 or BNP3, or the absence of the ribonucleic acid encoding BNP2 or BNP3. The heart condition can be heart failure, unstable angina, acute myocardial infarction, or hypertension.

In another aspect, the invention features a method for treating a heart condition in a mammal. The method includes administering a polypeptide or a nucleic acid to the mammal under conditions wherein the severity of a symptom of the heart condition is reduced. The polypeptide includes an amino acid sequence selected from the group consisting of the amino acid sequence of SEQ ID NO:1, 2, 3, 4, 35, or 36; a sequence having at least 6 contiguous residues of the amino acid sequence of SEQ ID NO:1 or SEQ ID NO:2; a sequence having at least 65% sequence identity to the amino acid sequence of SEQ ID NO:1 or SEQ ID NO:2; and a sequence having at least 65% sequence identity to a fragment of SEQ ID NO:1 or SEQ ID NO:2 at least six contiguous residues in length. The amino acid sequence can have at least 75% (e.g., 80, 90, or 95%) sequence identity to the amino acid sequence of SEQ ID NO:1 or SEQ ID NO:2 or at least 75% (e.g., 80, 90, or 95%) sequence identity to a fragment of SEQ ID NO:1 or SEQ ID NO:2 at least 6 contiguous residues in length. In some embodiments, the polypeptide can include the amino acid sequence of SEQ ID NO:35 or SEQ ID NO:36. The nucleic acid contains a sequence encoding a polypeptide described above. The polypeptide can be encoded by the nucleic acid sequence of SEQ ID NO:5; the nucleic acid sequence of nucleotides 383 to 489 of SEQ ID NO:5; the nucleic acid sequence of SEQ ID NO:6; or the nucleic acid sequence of nucleotides 388 to 432 of SEQ ID NO:6. The heart condition can be heart failure, unstable angina, acute myocardial infarction, and/or hypertension.

In another aspect, the invention features a method for treating a kidney condition in a mammal. The method includes administering a polypeptide or a nucleic acid to the mammal under conditions wherein the severity of a symptom of the kidney condition is reduced. The polypeptide includes an amino acid sequence selected from the group consisting of the amino acid sequence of SEQ ID NO:1, 2, 3, 4, 35, or 36; a sequence having at least 6 contiguous residues of the amino acid sequence of SEQ ID NO:1 or SEQ ID NO:2; a sequence having at least 65% sequence identity to the amino acid sequence of SEQ ID NO:1 or SEQ ID NO:2; and a sequence having at least 65% sequence identity to a fragment of SEQ ID NO:1 or SEQ ID NO:2 at least six contiguous residues in length. The amino acid sequence can have at least 75% (e.g., 80, 90, or 95%) sequence identity to the amino acid sequence of SEQ ID NO:1 or SEQ ID NO:2 or at least 75% (e.g., 80, 90, or 95%) sequence identity to a fragment of SEQ ID NO:1 or SEQ ID NO:2 at least 6 contiguous residues in length. In some embodiments, the polypeptide can include the amino acid sequence of SEQ ID NO:35 or SEQ ID NO:36. The nucleic acid contains a sequence encoding a polypeptide described above. The polypeptide can be encoded by the nucleic acid sequence of SEQ ID NO:5; the nucleic acid sequence of nucleotides 383 to 489 of SEQ ID NO:5; the nucleic acid sequence of SEQ ID NO:6; or the nucleic acid sequence of nucleotides 388 to 432 of SEQ ID NO:6. The kidney condition can be kidney failure.

In another aspect, the invention features a method for increasing cGMP within a mammal. The method includes administering a polypeptide described herein or a nucleic acid encoding said polypeptide to the mammal under conditions wherein the level of cGMP within the mammal is increased.

In another aspect, the invention features a method for dilating an artery within a mammal. The method includes administering a polypeptide described herein or a nucleic acid encoding said polypeptide to the mammal under conditions wherein said artery dilates.

In another aspect, the invention features a method for increasing diuresis and/or natriuresis in a mammal. The method includes administering a polypeptide described herein or a nucleic acid encoding said polypeptide to the mammal under conditions wherein diuresis and/or natriuresis increases.

In another aspect, the invention features a purified antibody. The antibody binds to a BNP2 polypeptide, and does not bind to a BNP polypeptide consisting of the sequence set forth SEQ ID NO:16 or to a BNP3 polypeptide consisting of the sequence set forth in SEQ ID NO:4. The BNP2 polypeptide can contain the sequence set forth in SEQ ID NO:1. The antibody can be a monoclonal antibody.

In another aspect, the invention features a purified antibody. The antibody binds to a BNP3 polypeptide, and does not bind to a BNP polypeptide consisting of the sequence set forth in SEQ ID NO:16 or to a BNP2 polypeptide consisting of the sequence set forth in SEQ ID NO:3. The BNP3 polypeptide can contain the sequence set forth in SEQ ID NO:2. The antibody can be a monoclonal antibody.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 1A and 1B are the nucleotide and amino acid sequences of human BNP2 (SEQ ID NO:5 and SEQ ID NO:3, respectively), and the nucleotide and amino acid sequences of dog BNP2 (SEQ ID NO:38 and SEQ ID NO:14, respectively), as indicated. The underlined sequences represent the mature peptides. SEQ ID NO:1, shown in FIG. 1A, is the C-terminal sequence of the human BNP2 polypeptide.

FIG. 2 is the nucleotide sequence (SEQ ID NO:6) and amino acid sequence (SEQ ID NO:4) of human BNP-3. The underlined sequence represents the mature peptide. SEQ ID NO:2 is the C-terminal sequence of the human BNP3 polypeptide.

FIG. 4 contains the amino acid sequences of BNP (SEQ ID NO:16); DNP (SEQ ID NO:17); ANP (SEQ ID NO:18); and CNP (SEQ ID NO:1.9).

DETAILED DESCRIPTION

Figure 3:
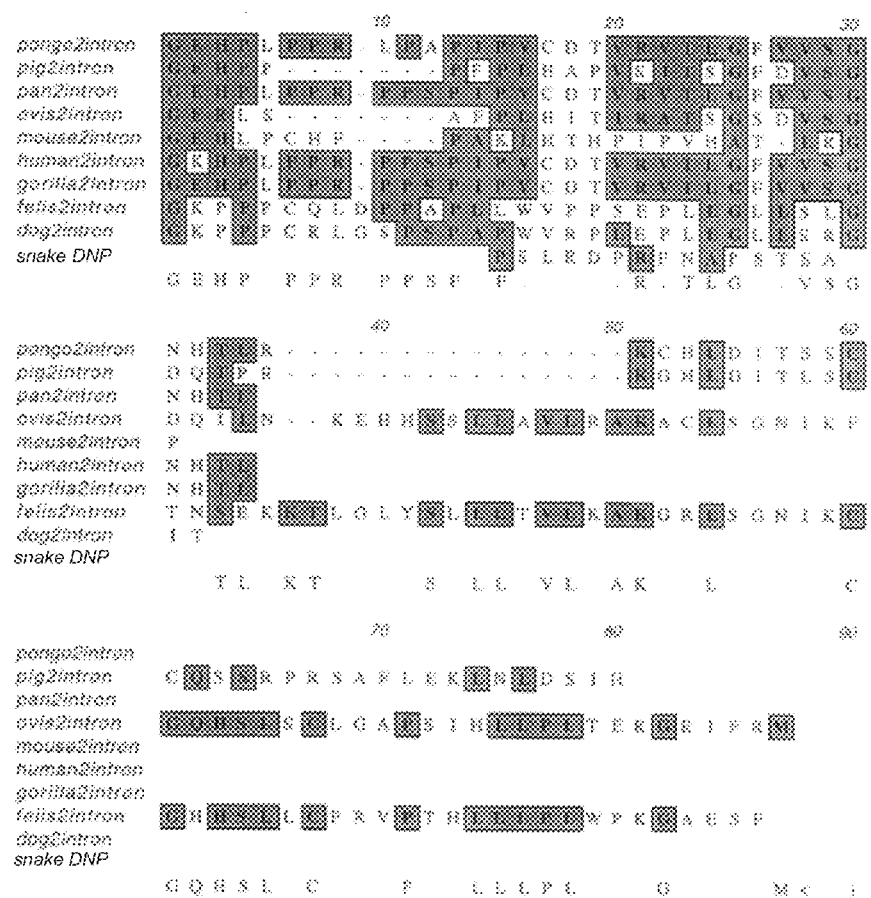
FIG. 3 is an alignment of C-terminal BNP2 polypeptide sequences from orangutan (SEQ ID NO:7); pig (SEQ ID NO:8); chimpanzee (SEQ ID NO:9); sheep (SEQ ID NO:10); mouse (SEQ ID NO:11); human (SEQ ID NO:1); gorilla (SEQ ID NO:12); cat (SEQ ID NO:13); dog (SEQ ID NO:37); and snake (SEQ ID NO:15).

In general, the invention provides isoforms BNP, including BNP2 and BNP3 polypeptides, and methods of using the isoforms as markers for various heart conditions, including heart failure, hypertension, unstable angina, sudden cardiac death, and acute myocardial infarction, as well as renal failure. As described herein, BNP2 and BNP3 are present in biological samples from patients with failing hearts but are absent or at low levels in biological samples from control patients. Consequently, the presence or level of BNP2 or BNP2 can be detected in biological samples and used to diagnose heart conditions, monitor treatment for heart conditions, or track progression of heart disease. The presence or level of BNP isoforms can be assessed by either measuring BNP2 or BNP3 polypeptides or ribonucleic acids encoding BNP2 or BNP3 as described below.

In addition, the polypeptides provided herein (e.g., BNP2 and BNP3) as well as nucleic acids encoding such polypeptides may be used as therapeutics for the treatment of heart conditions and/or kidney conditions. Therapeutic effects of BNP2 and BNP3 may be similar to BNP, which is a balanced vasodilator with no inotropic nor chronotropic properties. Intravenous therapy with recombinant BNP (Nesiritide, Natrecor®) significantly decreases pulmonary capillary wedge pressure and systemic vascular resistance and increases cardiac index. BNP is not pro-arrhythmic and has no effect on heart rate. Burger and Burger, *Curr. Opin. Investig. Drugs* 2(7):929-35 (2001).

In some embodiments, the polypeptides provided herein (e.g., BNP2 and BNP3) or nucleic acids encoding such polypeptides can be used to stimulate cGMP and/or vasodilate arteries in a mammal. In addition, the polypeptides provided herein (e.g., BNP2 and BNP3) or nucleic acids encoding such polypeptides can be used to treat hypertension, pulmonary hypertension, and/or congestive heart failure. In other embodiments, the polypeptides provided herein (e.g., BNP2 and BNP3) or nucleic acids encoding such polypeptides can be used increase diuresis and/or natriuresis in a mammal. For example, a BNP2 or BNP3 polypeptide can be administered to a mammal to increase urinary flow and urinary excretion of sodium. In addition, the polypeptides provided herein (e.g., BNP2 and BNP3) or nucleic acids encoding such polypeptides can be used to treat a fluid overload state (e.g., congestive heart failure, liver failure, and kidney failure) and/or to treat a sodium overloaded state (e.g., congestive heart failure).

BNP Isoforms

The invention features purified isoforms of BNP. As used herein, the term "purified" with reference to an isoform of BNP means that the polypeptide is substantially free of other polypeptides, lipids, carbohydrates, and nucleic acid with which it is naturally associated. Thus, a purified polypeptide is any polypeptide that is removed from its natural environment and is at least 60 percent pure. A purified polypeptide can be at least about 65, 70, 75, 80, 85, 90, 95, or 99 percent pure. Typically, a purified polypeptide will yield a single major band on a non-reducing polyacrylamide gel.

An isoform of BNP refers to any polypeptide that (1) has the amino acid sequence set forth in SEQ ID NO:1, 2, 3, 4, 14, 35, or 36, (2) contains an amino acid sequence having a length of about 6, 7, 8, 9, 10, 11, 12, 13, 14, or more amino acid residues with at least about 45, 50, 55, 60, 65, 70, 75, 80, 85, 90, 95, or more percent identity over that length to the amino acid sequence set forth in SEQ ID NO:1 or 2, or (3) contains about 6, 7, 8, 9, 10, 11, 12, 13, 14 or more consecutive amino acid residues encoded by a nucleic acid sequence that hybridizes, under hybridization conditions (see below), to the sense or antisense strand of a nucleic acid encoding the sequence set forth in SEQ ID NO:1 or 2. For example, a polypeptide can contain an amino acid sequence of 10, 15, 20, 25, 30 or more residues in length and have at least 45% identity with the amino acid sequence of SEQ ID NO:1, which contains the 33 amino acid C-terminal fragment of human BNP2 (see FIG. 1A). The full-length amino acid sequence of human BNP2 is set forth in SEQ ID NO:3 and the sequence of the mature BNP2 polypeptide is set forth in SEQ ID NO:36 (see the underlined sequence in FIG. 1A). SEQ ID NO:2 contains the 14 amino acid C-terminal fragment of human BNP3 (see FIG. 2). The full-length amino acid sequence of human BNP3 is set forth in SEQ ID NO:4 while the sequence of the mature BNP3 polypeptide is set forth in SEQ ID NO:35 (see underlined sequence in FIG. 2).

Non-limiting examples of polypeptide sequences that have at least 45% identity to the polypeptide sequence set forth in SEQ ID NO:1 include the C-terminal BNP2 polypeptide sequences depicted in FIG. 3. For example, the C-terminal BNP2 sequences from human (SEQ ID NO:1) and pig (SEQ ID NO:8) have about 48% identity. The C-terminal BNP2 sequences from human (SEQ ID NO:1) and mouse (SEQ ID NO:11) have about 67% identity. The C-terminal BNP2 sequences from human (SEQ ID NO:1) and orangutan (SEQ ID NO:7) have about 91% identity. The C-terminal BNP2 sequences from human (SEQ ID NO:1), chimpanzee (SEQ ID NO:9), and gorilla (SEQ ID NO:12) have about 97% identity.

The length and percent identity over that length for any amino acid sequence is determined as follows. First, an amino acid sequence is compared to the identified amino acid sequence (e.g., SEQ ID NO:1) using the BLAST 2 Sequences (Bl2seq) program from the stand-alone version of BLASTZ containing BLASTN version 2.0.14 and BLASTP version 2.0.14. This stand-alone version of BLASTZ can be obtained from the world wide web at Fish & Richardson P.C.'s web site ("fr" dot "com/blast/") or at the U.S. government's National Center for Biotechnology Information web site ("ncbi" dot "nlm" dot "nih" dot "gov"). The stand-alone version of BLASTZ also can be obtained from the library at the State University of New York at Old Westbury under the call number QH 447.M6714. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences.

To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the target sequence shares homology with any portion of the identified sequence, then the designated output file will present those regions of homology as aligned sequences. If the target sequence does not share homology with any portion of the identified sequence, then the designated output file will not present aligned sequences. Once aligned, a length is determined by counting the number of consecutive amino acid residues from the target sequence presented in alignment with sequence from the identified sequence (e.g., SEQ ID NO:1) starting with any matched position and ending with any other matched position. A matched position is any position where an identical amino acid residue is presented in both the target and identified sequence. Gaps presented in the target sequence are not counted since gaps are not amino acid residues. Likewise, gaps presented in the identified sequence are not counted since target sequence amino acid residues are counted, not amino acid residues from the identified sequence.

The percent identity over a determined length is determined by counting the number of matched positions over that length and dividing that number by the length followed by multiplying the resulting value by 100. For example, if (1) a 50 amino acid target sequence is compared to the sequence set forth in SEQ ID NO:1, (2) the Bl2seq program presents 20 amino acid residues from the target sequence aligned with a region of the sequence set forth in SEQ ID NO:1 where the first and last amino acid residues of that 20 amino acid region are matches, and (3) the number of matches over those 20 aligned amino acids is 18, then the 50 amino acid target sequence contains a length of 20 and a percent identity over that length of 90 (i.e., 18÷20*100=90).

It will be appreciated that a single amino acid target sequence that aligns with the sequence set forth in SEQ ID NO:1 can have many different lengths with each length having its own percent identity. It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It is also noted that the length value will always be an integer.

The hybridization conditions can be moderately or highly stringent hybridization conditions. For the purpose of this invention, moderately stringent hybridization conditions mean the hybridization is performed at about 42° C. in a hybridization solution containing 25 mM $KPO_4$ (pH 7.4), 5×SSC, 5× Denhart's solution, 50 μg/mL denatured, sonicated salmon sperm DNA, 50% formamide, 10% Dextran sulfate, and 1-15 ng/mL probe (about $5×10^7$ cpm/μg), while the washes are performed at about 50° C. with a wash solution containing 2×SSC and 0.1% sodium dodecyl sulfate.

Highly stringent hybridization conditions mean the hybridization is performed at about 42° C. in a hybridization solution containing 25 mM $KPO_4$ (pH 7.4), 5×SSC, 5× Denhart's solution, 50 μg/mL denatured, sonicated salmon sperm DNA, 50% formamide, 10% Dextran sulfate, and 1-15 ng/mL probe (about $5×10^7$ cpm/μg), while the washes are performed at about 65° C. with a wash solution containing 0.2×SSC and 0.1% sodium dodecyl sulfate.

In some embodiments, an isoform of BNP can stimulate production of cGMP in human umbilical vascular endothelial cells (HUVEC). Intracellular cGMP production can be assayed using, for example, the BIOTRACK cGMP enzyme immunoassay kit (Amersham Pharmacia Biotech). In other embodiments, the isoforms of BNP is vasoactive. Vasoactivity can be assessed by determining responsivity of a blood vessel (e.g., a carotid artery in an organ chamber) to the isoform.

Isoforms of BNP can be obtained by extraction from a natural source (e.g., from isolated cells, tissues or bodily fluids), by expression of a recombinant nucleic acid encoding the polypeptide, or by chemical synthesis. For example, standard recombinant technology using expression vectors encoding isoforms of BNP (as described below) can be used. The resulting polypeptides then can be purified using, for example, affinity chromatographic techniques and HPLC. The extent of purification can be measured by any appropriate method, including but not limited to: column chromatography, polyacrylamide gel electrophoresis, or high-performance liquid chromatography. Isoforms of BNP can be "engineered" to contain a tag sequence that allows the polypeptide to be purified (e.g., captured onto an affinity matrix). For example, a tag such as c-myc, hemagglutinin, polyhistidine, or FLAG™ epitope tag (Kodak) can be used to aid polypeptide purification. Such tags can be inserted anywhere within the polypeptide including at either the carboxyl or amino termini. Other fusions that can be used include enzymes that aid in the detection of the polypeptide, such as alkaline phosphatase.

Chimeric natriuretic polypeptides can be produced that contain two regions, a first region that includes the N-terminus and ring structure of a mature natriuretic polypeptide (e.g., BNP, DNP, ANP, or CNP) and a second region that includes the C-terminal portion of a BNP isoform. The N-terminus and ring structure of BNP includes residues 1 to 27 of SEQ ID NO:16 while the N-termini and ring structures of DNP and ANP include residues 1 to 23 of SEQ ID NO:17 and SEQ ID NO:18, respectively. The sequences of BNP, DNP, ANP, and CNP are presented in FIG. 4. In other embodiments, the first region can contain the N-terminus and ring structure of a naturietic polypeptide with one to five amino acid substitutions. Suitable C-terminal portions of a BNP isoform have at least 45% identity to the amino acid sequences of SEQ ID NO:1 and 2, as discussed above. The C-terminal portion can have the sequence set forth in SEQ ID NO:20 (described below). Chimeric polypeptides can have biological activities of naturietic peptides, including the ability to stimulate cyclic GMP production in cells or vasoactivity.

In some embodiments, a polypeptide of the invention can have the sequence set forth in the formula: Gly-$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-$Xaa_{18}$-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$Xaa_{27}$-Gly-$Xaa_{29}$-$Xaa_{30}$-$Xaa_{31}$-$Xaa_{32}$, (SEQ ID NO:20), wherein $Xaa_1$ is Glu or Lys; $Xaa_2$ is Pro, His, or Arg; $Xaa_3$ is Pro or Leu; $Xaa_4$ is Pro, Leu, or Ser; $Xaa_5$ is Cys or Pro; $Xaa_6$ is Pro, His, Gln, or Arg; $Xaa_7$ is Arg, Phe, or Leu; $Xaa_8$ is Asp, Gly, or absent; $Xaa_9$ is Ser, Pro, or Leu; $Xaa_{10}$ is Pro or absent; $Xaa_{11}$ is Ser, Ala, or absent; $Xaa_{12}$ is Pro or Ala; $Xaa_{13}$ is Ala, Phe, Ile, or Leu; $Xaa_{14}$ is Pro, Lys, or Leu; $Xaa_{15}$ is Val, Leu, or Trp; $Xaa_{16}$ is Cys; His, or Val; $Xaa_{17}$ is Asp, Ala, Ile, Thr, Pro, or Arg; $Xaa_{18}$ is Thr, Pro, or His; $Xaa_{19}$ is Val, Ile, Pro, Val, Ser, or Leu; $Xaa_{20}$ is Arg, Ser, Ile, or Glu; $Xaa_{21}$ is Val, Ile, Ala, or Pro; $Xaa_{22}$ is Thr, Val, or Leu; $Xaa_{23}$ is Leu, Ser, or His; $Xaa_{24}$ is Gly or Ala; $Xaa_{25}$ is Phe, Ser, Thr, or Leu; $Xaa_{26}$ is Val, Asp, or Leu; $Xaa_{27}$ is Val, Leu, or Ser; $Xaa_{28}$ is Ser, Arg, or Leu; $Xaa_{29}$ is Asn, Asp, Pro, or Thr; $Xaa_{30}$ is His, Gln, Asn, or Thr; $Xaa_{31}$ is Thr, Ile, or Ser; and $Xaa_{32}$ is Pro, Leu, or Glu. The amino acids set forth at each position of SEQ ID NO:20 represent the residues that are present in naturally-occurring BNP2 polypeptides, including BNP2 from humans (SEQ ID NO:3); orangutan (SEQ ID NO:7), chimpanzee (SEQ ID NO:9); (SEQ ID NO:12); cat (SEQ ID NO:12); dog (SEQ ID NO:14); mouse (SEQ ID NO:11); sheep (SEQ ID NO:10); and pig (SEQ ID NO:8). A nucleic acid encoding such polypeptides can be produced as described below.

Polypeptides of the invention can be formulated as pharmaceutical compositions by admixture with pharmaceutically acceptable non-toxic excipients or carriers. Such compositions can be administered to a subject in need thereof in an amount effective to treat a heart condition or a kidney condition. Pharmaceutical compositions may be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Compositions for other routes of administration may be prepared as desired using standard methods.

Formulations for parenteral administration may contain as common excipients sterile water or saline, polyalkylene glycols such as polyethylene glycol, oils of vegetable origin, hydrogenated naphthalenes, and the like. In particular, biocompatible, biodegradable lactide polymer, lactide/glycolide copolymer, or polyoxyethylene-polyoxypropylene copolymers are examples of excipients for controlling the release of the polypeptide in vivo. Other suitable parenteral delivery systems include ethylene-vinyl acetate copolymer particles, osmotic pumps, implantable infusion systems, and liposomes. Formulations for inhalation administration may contain excipients such as lactose, if desired. Inhalation formulations may be aqueous solutions containing, for example, polyoxyethylene-9-lauryl ether, glycocholate and deoxycholate, or they may be oily solutions for administration in the form of nasal drops. If desired, the compounds can be formulated as gels to be applied intranasally. Formulations for parenteral administration may also include glycocholate for buccal administration For oral administration, tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulfate). Tablets can be coated by methods known in the art. Preparations for oral administration can also be formulated to give controlled release of the compound.

Nasal preparations can be presented in a liquid form or as a dry product. Nebulised aqueous suspensions or solutions can include carriers or excipients to adjust pH and/or tonicity.

Nucleic Acids Encoding Isoforms of MVP

The invention also features isolated nucleic acids that encode BNP polypeptides. The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid (e.g., a nucleic acid encoding the polypeptide of SEQ ID NO:20) can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence. A nucleic acid existing among hundreds to millions of other nucleic acids within, for example, cDNA libraries or genomic libraries, or gel slices containing a genomic DNA restriction digest, is not to be considered an isolated nucleic acid.

As used herein, the term "nucleic acid" refers to both RNA and DNA, including mRNA, cDNA, genomic DNA, synthetic (e.g., chemically synthesized) DNA, and nucleic acid analogs. The nucleic acid can be double-stranded or single-stranded, and where single-stranded, can be the sense strand or the antisense strand. In addition, nucleic acid can be circular or linear. Nucleic acid analogs can be modified at the base moiety, sugar moiety, or phosphate backbone to improve, for example, stability, hybridization, or solubility of a nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

Nucleic acids of the invention can have the sequence set forth in SEQ ID NOS: 5 or 6 (see FIGS. 1 and 2) or have a sequence having at least 45% identity (e.g., 45, 50, 55, 60, 65, 70, 75, 80, 85, 90, or 95 identity) to the sequence set forth in nucleotides 383 to 489 of SEQ ID NO:5 or nucleotides 388 to 432 of SEQ ID NO:6. Nucleotides 383 to 189 of SEQ ID NO:5 encode the amino acid sequence set forth in SEQ ID NO:1. Nucleotides 388 to 432 of SEQ ID NO:6 encode the amino acid sequence set forth in SEQ ID NO:2.

Sequence identity can be determined as described above. BLASTN is used to compare nucleic acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. The following command will generate an output file containing a comparison between two sequences: C:\Bl2seq -i c:\seq1.txt -j c:\seq2.txt -p blastn -o c:\output.txt -q −1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

Typically, isolated nucleic acids are at least 10 nucleotides in length (e.g., 10, 15, 20, 25, 30, 35, 40, 50, 75, 100, 200, 300, 350, 400, or more nucleotides in length). Nucleic acid molecules that are less than full-length can be useful, for example, as primers or probes for diagnostic purposes. Isolated nucleic acid molecules can be produced by standard techniques, including, without limitation, common molecular cloning and chemical nucleic acid synthesis techniques. For example, polymerase chain reaction (PCR) techniques can be used. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 15 to 50 nucleotides in length, but can range from 10 nucleotides to hundreds of nucleotides in length. For example, a primer can be 12, 15, 16, 17, 18, 19, 20, 21, 22, 23, 24, 25, 26, 27, 28, 29, 30, 35, 40, or 45 nucleotides in length. A primer can be purified from a restriction digest by conventional methods, or can be chemically synthesized. Primers typically are single-stranded for maximum efficiency in amplification, but a primer can be double-stranded. Double-stranded primers are first denatured (e.g., treated with heat) to separate the strands before use in amplification. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis *Genetic Engineering News* 12(9):1 (1992); Guatelli et al. (1990) *Proc. Natl. Acad. Sci. USA,* 87:1874-1878; and Weiss (1991) *Science* 254:1292.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids also can be obtained by mutagenesis. For example, the sequences depicted in FIG. 1, 2, or 3 can be mutated using standard techniques such as, for example, oligonucleotide-directed mutagenesis and/or site-directed mutagenesis through PCR. See, *Short Protocols in Molecular Biology*, Chapter 8, Green Publishing Associates and John Wiley & Sons, Edited by Ausubel et al., 1992. Examples of positions to be modified can be identified from the sequence alignment of FIG. 3.

Nucleic acids encoding a polypeptide provided herein can be formulated as pharmaceutical compositions by admixture with pharmaceutically acceptable non-toxic excipients or carriers. Such compositions can be administered to a subject in need thereof in an amount effective to treat a heart condition or a kidney condition.

Vectors and Host Cells

The invention also provides vectors containing nucleic acids such as those described above. As used herein, a "vector" is a replicon, such as a plasmid, phage, or cosmid, into which another DNA segment may be inserted so as to bring about the replication of the inserted segment. The vectors of the invention can be expression vectors. An "expression vector" is a vector that includes one or more expression control sequences, and an "expression control sequence" is a DNA sequence that controls and regulates the transcription and/or translation of another DNA sequence.

In the expression vectors of the invention, the nucleic acid is operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, poxviruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

The invention also provides host cells containing vectors of the invention. The term "host cell" is intended to include prokaryotic and eukaryotic cells into which a vector can be introduced. Any method can be used to introduce a vector into a cell. For example, calcium phosphate precipitation, electroporation, heat shock, lipofection, microinjection, and viral-mediated nucleic acid transfer can be used introduce isolated nucleic acid into cells. In addition, naked DNA can be delivered directly to cells in vivo as described elsewhere (U.S. Pat. Nos. 5,580,859 and 5,589,466).

Methods of Using BNP2 or BNP3 to Diagnose Heart Conditions

In general, methods of the invention include detecting the presence or absence of an isoform of BNP in a biological sample from a patient (e.g., a human patient) and diagnosing the patient based on the presence or absence of the BNP isoform. In other embodiments, the level of the BNP isoform can be determined and compared to the level of the isoform from a control population (e.g., the average level of BNP2 from a plurality of control subjects without heart conditions). Thus, the presence of an isoform of BNP or an increase in the level of the isoform relative to that of the control population is indicative of a heart condition. Suitable biological samples for detecting isoforms of BNP include, for example, blood (including whole blood, plasma, and serum), urine, saliva, heart tissue, and circulating cells.

Additional factors that can be considered when diagnosing heart conditions can include, for example, family history or other genetic factors and the levels of other cardiac markers such as troponin I or T, high sensitive C-reactive protein (hs-CRP), creatine kinase (CK), CK-MB, creatinine, or myoglobin. In general, myoglobin is not cardiac specific, but is released from infracted myocardium at an early stage (about 2-3 hours post infarction) and returns to normal within about 24 hours. Cardiac isoforms of troponin I and troponin T are specific, but appear in the circulation later than myoglobin (5 to 48 hours post infarction). Myocardial tissue contains one isoform of CK-MB, while skeletal tissue has different isoforms. Antibodies having specific binding affinity for such cardiac markers are available commercially.

The presence, absence, or level of a BNP isoform in a subject also can be used to monitor treatment (e.g., treatment with an ACE inhibitor or β blocker) for a heart condition. For example, the subject's baseline level of a BNP isoform before treatment can be compared to the level of the isoform at various time points after treatment (e.g., one or more hours, days, weeks, or months after treatment). A decrease in the level of the BNP isoform relative to the baseline level is indicative of a positive response to treatment. Treatment can be monitored based on a combination of the presence, absence, or level of the BNP isoform and the level of other cardiac markers as described above.

Detecting Isoforms of BNP

Isoform of BNP such as BNP2 or BNP3 can be detected, for example, immunologically using one or more antibodies. As used herein, the terms "antibody" or "antibodies" include intact molecules as well as fragments thereof that are capable of binding to an epitopic determinant of a BNP isoform. The term "epitope" refers to an antigenic determinant on an antigen to which the paratope of an antibody binds. Epitopic determinants usually consist of chemically active surface groupings of molecules such as amino acids or sugar side chains, and typically have specific three-dimensional structural characteristics, as well as specific charge characteristics. Epitopes generally have at least five contiguous amino acids (a continuous epitope), or alternatively can be a set of non-contiguous amino acids that define a particular structure (e.g., a conformational epitope). The terms "antibody" and "antibodies" include polyclonal antibodies, monoclonal antibodies, humanized or chimeric antibodies, single chain Fv antibody fragments, Fab fragments, and $F(ab)_2$ fragments. Polyclonal antibodies are heterogenous populations of antibody molecules that are contained in the sera of the immunized animals. Monoclonal antibodies are homogeneous populations of antibodies to a particular epitope of an antigen.

Antibody fragments that have specific binding affinity for an isoform of BNP can be generated by known techniques. For example, F(ab')2 fragments can be produced by pepsin digestion of the antibody molecule; Fab fragments can be generated by reducing the disulfide bridges of F(ab')2 fragments. Alternatively, Fab expression libraries can be constructed. See, for example, Huse et al., *Science*, 216:1275 (1989). Once produced, antibodies or fragments thereof are tested for recognition of a BNP isoform by standard immunoassay methods including ELISA techniques, radioimmunoassays, and Western blotting. See, *Short Protocols in Molecular Biology*, Chapter 11, Green Publishing Associates and John Wiley & Sons, Edited by Ausubel, F. M et al., 1992.

In immunological assays, an antibody having specific binding affinity for an isoform of BNP or a secondary antibody that binds to such an antibody can be labeled, either directly or indirectly. Suitable labels include, without limitation, radionuclides (e.g. $^{125}I$, $^{131}I$, $^{35}S$, $^{3}H$, $^{32}P$, $^{33}P$, or $^{14}C$), fluorescent moieties (e.g., fluorescein, FITC, PerCP, rhodamine, or PE), luminescent moieties (e.g., QDOT™ nanoparticles supplied by the Quantum Dot Corporation, Palo Alto, Calif.), compounds that absorb light of a defined wavelength, or enzymes (e.g., alkaline phosphatase or horseradish peroxidase). Antibodies can be indirectly labeled by conjugation with biotin then detected with avidin or streptavidin labeled with a molecule described above. Methods of detecting or quantifying a label depend on the nature of the label and are known in the art. Examples of detectors include, without limitation, x-ray film, radioactivity counters, scintillation counters, spectrophotometers, colorimeters, fluorometers, luminometers, and densitometers. Combinations of these approaches (including "multi-layer" assays) familiar to those in the art can be used to enhance the sensitivity of assays.

Immunological assays for detecting an isoform of BNP can be performed in a variety of known formats, including sandwich assays, competition assays (competitive RIA), or bridge immunoassays. See, for example, U.S. Pat. Nos. 5,296,347; 4,233,402; 4,098,876; and 4,034,074. Methods of detecting an isoform of BNP generally include contacting a biological sample with an antibody that binds to the isoform of BNP and detecting binding of the isoform of BNP to the antibody. For example, an antibody having specific binding affinity for an isoform of BNP can be immobilized on a solid substrate by any of a variety of methods known in the art and then exposed to the biological sample. Binding of the BNP isoform to the antibody on the solid substrate can be detected by exploiting the phenomenon of surface plasmon resonance, which results in a change in the intensity of surface plasmon resonance upon binding that can be detected qualitatively or quantitatively by an appropriate instrument, e.g., a Biacore apparatus (Biacore International AB, Rapsgatan, Sweden). Alternatively, the antibody is labeled and detected as described above. A standard curve using known quantities of the isoform can be generated to aid in the quantitation of the levels of the isoform.

In other embodiments, a "sandwich" assay in which a capture antibody is immobilized on a solid substrate is used to detect the presence, absence, or level of an isoform of BNP. The solid substrate can be contacted with the biological sample such that any BNP2 or BNP3 in the sample can bind to the immobilized antibody. The presence, absence, or level of the BNP isoform bound to the antibody can be determined using a "detection" antibody having specific binding affinity for the isoform and the methods described above. In some embodiments, a capture antibody is used that has binding affinity for BNP as well as BNP2 and BNP3. In this embodiment, a detection antibody can be used that has specific binding affinity for BNP2 or BNP3. It is understood that in sandwich assays, the capture antibody should not bind to the same epitope (or range of epitopes in the case of a polyclonal antibody) as the detection antibody. Thus, if a monoclonal antibody is used as a capture antibody, the detection antibody can be another monoclonal antibody that binds to an epitope that is either completely physically separated from or only partially overlaps with the epitope to which the capture monoclonal antibody binds, or a polyclonal antibody that binds to epitopes other than or in addition to that to which the capture monoclonal antibody binds. If a polyclonal antibody is used as a capture antibody, the detection antibody can be either a monoclonal antibody that binds to an epitope that is either completely physically separated from or partially overlaps with any of the epitopes to which the capture polyclonal antibody binds, or a polyclonal antibody that binds to epitopes other than or in addition to that to which the capture polyclonal antibody binds. Sandwich assays can be performed as sandwich ELISA assays, sandwich Western blotting assays, or sandwich immunomagnetic detection assays.

Suitable solid substrates to which an antibody (e.g., a capture antibody) can be bound include, without limitation, microtiter plates, tubes, membranes such as nylon or nitrocellulose membranes, and beads or particles (e.g., agarose, cellulose, glass, polystyrene, polyacrylamide, magnetic, or magnetizable beads or particles). Magnetic or magnetizable particles can be particularly useful when an automated immunoassay system is used.

Antibodies having specific binding affinity for an isoform of BNP can be produced through standard methods. In general, a polypeptide can be recombinantly produced as described above, or can be purified from a biological sample, and used to immunize host animals, including rabbits, chickens, mice, guinea pigs, or rats. For example, a polypeptide having the amino acid sequence set forth in SEQ ID NOS:1 or 2, or fragments thereof that are at least six amino acids in length, can be used to immunize an animal. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Monoclonal antibodies can be prepared using a BNP polypeptide and standard hybridoma technology. In particular, monoclonal antibodies can be obtained by any technique that provides for the production of antibody molecules by continuous cell lines in culture such as described by Kohler, G. et al., *Nature*, 256:495 (1975), the human B-cell hybridoma technique (Kosbor et al., *Immunology Today*, 4:72 (1983); Cole et al., *Proc. Natl. Acad. Sci. USA*, 80:2026 (1983)), and the EBV-hybridoma technique (Cole et al., "Monoclonal Antibodies and Cancer Therapy," Alan R. Liss, Inc., pp. 77-96 (1983)). Such antibodies can be of any immunoglobulin class including IgG, IgM, IgE, IgA, IgD, and any subclass thereof. The hybridoma producing the monoclonal antibodies of the invention can be cultivated in vitro and in vivo.

Alternative techniques for detecting BNP2 and BNP3 include mass-spectrophotometric techniques such as electrospray ionization (ESI), and matrix-assisted laser desorption-ionization (MALDI). See, for example, Gevaert et al., *Electrophoresis* 22(9):1645-51, 2001; Chaurand et al. *J Am Soc Mass Spectrom* 10(2):91-103, 1999. Mass spectrometers useful for such applications are available from Applied Biosystems (Foster City, Calif.); Bruker Daltronics (Billerica, Mass.); and Amersham Pharmacia (Sunnyvale, Calif.).

Detecting Nucleic Acids Encoding Isoforms of BNP

Any one of a number of clinical diagnostic techniques can be used to detect ribonucleic acids encoding an isoform of BNP. Hybridization can be performed on a solid substrate such as a nylon membrane (e.g., a macroarray) or a microarray (e.g., a microchip) or in solution (e.g., ORIGEN technology). In some embodiments, nucleic acid based methods can include an amplification step using, for example, PCR. Template nucleic acid need not be purified for PCR; it can be a minor fraction of a complex mixture, such as a cell lysate. Template DNA or RNA can be extracted from a biological sample using routine techniques.

Once a PCR amplification product is generated, it can be detected by, for example, hybridization using FRET technology. FRET technology (see, for example, U.S. Pat. Nos. 4,996,143, 5,565,322, 5,849,489, and 6,162,603) is based on the concept that when a donor fluorescent moiety and a corresponding acceptor fluorescent moiety are positioned within a certain distance of each other, enemy transfer taking place between the two fluorescent moieties can be visualized or otherwise detected and quantitated. Two oligonucleotide probes, each containing a fluorescent moiety, can hybridize to an amplification product at particular positions determined by the complementarity of the oligonucleotide probes to the target nucleic acid sequence. Upon hybridization of the oligonucleotide probes to the amplification product at the appropriate positions, a FRET signal is generated. Hybridization temperatures and times can range from about 35° C. to about 65° C. for about 10 seconds to about 1 minute. Detection of FRET can occur in real-time, such that the increase in an amplification product after each cycle of a PCR assay is detected and, in some embodiments, quantified.

Fluorescent analysis and quantification can be carried out using, for example, a photon counting epifluorescent microscope system (containing the appropriate dichroic mirror and filters for monitoring fluorescent emission in a particular range of wavelengths), a photon counting photomultiplier system, or a fluorometer. Excitation to initiate energy transfer can be carried out with an argon ion laser, a high intensity mercury arc lamp, a fiber optic light source, or another high intensity light source appropriately filtered for excitation in the desired range.

Fluorescent moieties can be, for example, a donor moiety and a corresponding acceptor moiety. As used herein with respect to donor and corresponding acceptor fluorescent moieties, "corresponding" refers to an acceptor fluorescent moiety having an emission spectrum that overlaps the excitation spectrum of the donor fluorescent moiety. The wavelength maximum of the emission spectrum of an acceptor fluorescent moiety typically should be at least 100 nm greater than the wavelength maximum of the excitation spectrum of the donor fluorescent moiety, such that efficient non-radiative enemy transfer can be produced there between.

Fluorescent donor and corresponding acceptor moieties are generally chosen for (a) high efficiency Förster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen with an excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC™-Red 640, LC™-Red 705, Cy5, Cy5.5, Lissamine rhodamine B sulfonyl chloride, tetramethyl rhodamine isothiocyanate, rhodamine×isothiocyanate, erythrosine isothiocyanate, fluorescein, diethylenetriamine pentaacetate, and other chelates of Lanthanide ions (e.g., Europium, or Terbium). Donor and acceptor fluorescent moieties can be obtained from, for example, Molecular Probes, Inc. (Eugene, Oreg.) or Sigma Chemical Co. (St. Louis, Mo.).

Donor and acceptor fluorescent moieties can be attached to probe oligonucleotides via linker arms. The length of each linker arm is important, as the linker arms will affect the distance between the donor and acceptor fluorescent moieties. The length of a linker arm for the purpose of the present invention is the distance in Angstroms (Å) from the nucleotide base to the fluorescent moiety. In general, a linker arm is from about 10 to about 25 Å in length. The linker arm may be of the kind described, for example, in WO 84/03285. WO 84/03285 also discloses methods for attaching linker arms to a particular nucleotide base, as well as methods for attaching fluorescent moieties to a linker arm.

An acceptor fluorescent moiety such as an LC™-Red 640-NHS-ester can be combined with C6-Phosphoramidites (available from ABI (Foster City, Calif.) or Glen Research (Sterling, Va.)) to produce, for example, LC™-Red 640-Phosphoramidite. Linkers frequently used to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as fluorescein-CPG from BioGenex (San Ramon, Calif.)), or 3'-amino-CPG's that require coupling of a fluorescein-NHS-ester after oligonucleotide synthesis.

Using commercially available real-time PCR instrumentation (e.g., LightCycler™, Roche Molecular Biochemicals, Indianapolis, Ind.), PCR amplification, detection, and quantification of an amplification product can be combined in a single closed cuvette with dramatically reduced cycling time. Since detection and quantification occur concurrently with amplification, real-time PCR methods obviate the need for manipulation of the amplification product, and diminish the risk of cross-contamination between amplification products. Real-time PCR greatly reduces turn-around time and is an attractive alternative to conventional PCR techniques in the clinical laboratory or in the field.

Control samples can be included within each thermocycler run. Positive control samples can amplify a nucleic acid control template (e.g., a nucleic acid other than a target nucleic acid) using, for example, control primers and control probes. Positive control samples also can amplify, for example, a plasmid construct containing a control nucleic acid template. Such a plasmid control can be amplified internally (e.g., within the sample) or in a separate sample run side-by-side with the test samples. Each thermocycler run also should include a negative control that, for example, lacks the target template DNA. Such controls are indicators of the success or failure of the amplification, hybridization and/or FRET reaction. Therefore, control reactions can readily determine, for example, the ability of primers to anneal with sequence-specificity and to initiate elongation, as well as the ability of probes to hybridize with sequence-specificity and for FRET to occur.

Another FRET format utilizes TAQMAN® gene expression technology to detect the presence, absence, or level of an amplification product, and hence, the presence, absence, or level of nucleic acid encoding an isoform of BNP. TAQMAN® gene expression technology utilizes one single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' exonuclease activity of the Taq Polymerase during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems, Foster City, Calif.) uses TAQMAN® gene expression technology, and is suitable for performing the methods described herein for detecting isoforms of BNP. Information on PCR amplification and detection using an ABI PRISM® 7700 system can be found at the website of Applied Biosystems.

Molecular beacons in conjunction with FRET also can be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

As an alternative to FRET, amplification product can be detected using, for example, a fluorescent DNA binding dye (e.g., SYBRGREENI® nucleic acid dye or SYBRGOLD® nucleic acid dye (Molecular Probes)). Upon interaction with an amplification product, such DNA binding dyes emit a fluorescent signal after excitation with light at a suitable wavelength. A double-stranded DNA binding dye such as a nucleic acid intercalating dye also can be used. When double-stranded DNA binding dyes are used, a melting curve analysis usually is performed for confirmation of the presence of the amplification product.

Articles of Manufacture

A BNP isoform, a nucleic acid encoding a BNP isoform, or an antibody having specific binding affinity for an isoform of BNP (e.g., BNP2 or BNP3) can be combined with packaging material and sold as a kit. Such kits can be useful for diagnosing heart conditions, monitoring treatment of heart conditions, monitoring progression of heart disease, or treating heart or kidney conditions. Components and methods for producing articles of manufactures are well known. The articles of manufacture may combine one or more polypeptides, nucleic acids, or antibodies as described herein. In addition, the articles of manufacture may further include reagents such as secondary antibodies, anti-BNP antibodies, buffers, indicator molecules, solid phases (e.g., beads) and/or other useful agents for diagnosing heart conditions, monitoring treatment of heart conditions, or monitoring progression of heart disease. An antibody can be in a container, such as a plastic, polyethylene, polypropylene, ethylene, or propylene vessel that is either a capped tube or a bottle, or can be included on a solid phase, e.g., a handheld device for bedside testing that includes an antibody (e.g., an anti-BNP2 or BNP3 antibody). Instructions describing how the various reagents are effective for treating heart or kidney conditions, monitoring treatment of heart conditions, or monitoring progression of heart disease also may be included in such kits.

The invention will be further described in the following examples, which do not limit the scope of the invention described in the claims.

EXAMPLES

Example 1

Identification of Brain Natriuretic Peptide-2 (BNP-2)

It was determined that intron 2 of the BNP genomic sequence encoded a polypeptide having homology to the C-terminal of the snake DNP polypeptide. To determine if the polypeptide encoded by intron 2 was expressed, Northern blotting was performed using cellular RNA isolated from kidney, brain, and heart (left ventricles and atria) tissue of patients with and without heart failure. Approximately 5 μg of RNA was electrophoresed through a 1% agarose gel containing formaldehyde and transferred to a nylon membrane. Northern blotting was performed using the NORTHERNMAX™ hybridization kit from Ambion, Inc. (Austin, Tex.), according to the manufacturer's instructions. The membranes were UV autocross-linked, prehybridized at 42° C. for 1 hour, and hybridized at 42° C. overnight with a labeled probe containing the second intron sequence. The probe was labeled with $^{32}$P using the Random Primers DNA Labeling System (Gibco BRL). The membranes were washed twice in low stringency buffer (provided in NORTHERNMAX™ hybridization kit, equivalent to 2×SSC, 0.1% SDS or 2×SSPE, 0.1% SDS) at room temperature, five minutes per wash, then washed twice in a high stringency buffer (provided in NORTHERNMAX™ hybridization kit, equivalent to 0.1× SSC, 0.1% SDS or 0.1×SSPE, 0.1% SDS) at 42° C., 15 minutes per wash. Hybridization signals on the blots were analyzed by autoradiography. Message for the second intron was detected in the left atrium of heart failure patients.

Example 2

Cloning of Human BNP-2

Total RNA was isolated from normal and heart failure human heart tissue using TRIZOL® Reagent (Gibco BRL), a monophasic solution of phenol and guanidine isothiocyanate. Complementary DNA (cDNA) was produced using an oligo (dT) primer and the THERMOSCRIPT™ RT-PCR Kit from Invitrogen Corp. (Carlsbad, Calif.) according to the manufacturer's instructions. RT-PCR was performed using a forward primer having the sequence: 5'-AGAC ATGGATCCCCAGACAG-3' (SEQ ID NO:21; 5' start codon is underlined) and a reverse primer having the sequence: 5'-CAAGAGGAAGCGATGTCCAG-3' (SEQ ID NO:22, positioned at nucleotides 113 to 133 in the second intron). After combining the cDNA and primers, an initial denaturation was performed at 94° C. for 4 min, followed by 35 cycles of denaturation at 94° C. for 30 secs, annealing at 52° C. for 1 min, and elongation at 72° C. for 45 sec then a final extension at 72° C. for 10 min. The resulting PCR product (~520 bp hBNP2 cDNA) was subcloned into Topo vector and sequenced for confirmation. The nucleic acid sequence of the hBNP2 cDNA is shown in FIG. 1A.

Example 3

Cloning of Dog BNP-2

Total RNA was isolated from normal and heart failure dog heart tissue using TRIZOL® Reagent (Gibco BRL), a monophasic solution of phenol and guanidine isothiocyanate. cDNA was made using an oligo(dT) primer and the THERMOSCRIPT™ RT-PCR Kit from Invitrogen Corp. (Carlsbad, Calif.) according to the manufacturer's instructions. RT-PCR was performed using a forward primer having the sequence: 5'-TTCTCTCCAGCGACATGGAG-3' (SEQ ID NO:23, 5' start codon is underlined) and a reverse primer having the sequence: 5'-GGACTCTTTCTGCTCCAAGG-3' (SEQ ID NO:24, positioned at nucleotides 288 to 308 in the second intron). After combining the cDNA and primers, an initial denaturation was performed at 94° C. for 4 min, followed by 35 cycles of denaturation at 94° C. for 30 secs, annealing at 55° C. for 1 min, and elongation at 72° C. for 45 sec then a final extension at 72° C. for 10 min. The resulting PCR product (~540 bp dBNP2 cDNA) was subcloned into Topo vector and sequenced for confirmation. The nucleic acid sequence of the dBNP cDNA is shown in FIG. 1B.

Example 4

Cloning of Human BNP-3

Total RNA was isolated from human heart tissue and cDNA were produced as described in Example 2, RT-PCR was performed using a forward primer having the sequence: 5'-AGAC<u>ATG</u>GATCCCCAGACAG-3' (SEQ ID NO:25, 5' start codon is underlined) and a reverse primers having the sequence: 5'-<u>TTTCTGCACC</u>ACTTTGCAGC-3' (SEQ ID NO:26, where the underlined portion of the primer is the 3' sequence of the second exon, and the non-underlined portion of the primer corresponds to position 289-300 of the second intron). After combining the cDNA and primers, an initial denaturation was performed at 94° C. for 4 min, followed by 35 cycles of denaturation at 94° C. for 30 secs, annealing at 60° C. for 1 min, and elongation at 72° C. for 45 sec then a final extension at 72° C. for 10 min. The resulting PCR product (~380 bp hBNP3 cDNA) was subcloned into Topo vector and sequenced for confirmation. The nucleic acid sequence of hBNP3 is shown in FIG. 2.

Example 5

Production of Anti-Human BNP2 Antibody

A peptide corresponding to the residues 27-60 of the mature human BNP2 peptide was synthesized by the Mayo protein core facility and used to produce polyclonal antibodies. Two rabbits were inoculated initially with 500 µg of the peptide plus Complete Freund's adjuvant followed by three booster inoculations of 250 µg of the peptide plus incomplete Freund's adjuvant. After each booster, sera were evaluated by Western-blotting. One of the rabbits (#1105) exhibited a specific response after immunization and continues to maintain a high antibody titer with periodic boosters.

The polyclonal anti-BNP2 antibody was used to detect BNP2 in human heart tissue. Two sets of slices of paraffin embedded, human heart, left atrial tissues (normal and heart failure) were de-paraffinized and treated with antigen retrieval buffer. One set of slices was incubated with 5 times diluted polyclonal rabbit anti-BNP2 antibody and the other with preimmune rabbit serum. Anti-rabbit biotin conjugate and streptavidin-alkaline phosphatase were used for color development. BNP2 was detected only in the heart tissue from the heart failure patient.

Example 6

Production of Anti-Human BNP3 Antibody

A peptide corresponding to the residues 27-41 of the mature human BNP3 peptide was synthesized by the Mayo protein core facility and used to produce polyclonal antibodies. Two rabbits were inoculated initially with 500 µg of the peptide plus Complete Freund's adjuvant followed by three booster inoculations of 250 µg of the peptide plus incomplete Freund's adjuvant. After, each booster, sera were evaluated by Western blotting. One of the rabbits (#1403) exhibited a specific response after immunization and continues to maintain a high antibody titer with periodic boosters.

The polyclonal anti-BNP32 antibody was used to detect BNP3 in human heart tissue. Two sets of slices of paraffin embedded, human heart, left atrial tissues (normal and heart failure) were de-paraffinized and treated with antigen retrieval buffer. One set of slices was incubated with 5 times diluted polyclonal rabbit anti-BNP3 antibody and the other with preimmune rabbit serum. Anti-rabbit biotin conjugate and streptavidin-alkaline phosphatase were used for color development. BNP3 was detected only in the heart tissue from the heart failure patient.

Example 7

Expression Levels of BNP Isoforms in Human Heart Tissue

Real-time PCR was used to assess the expression levels of BNP, BNP2, and BNP3 in both normal atria tissue and atria heart failure tissue. The level of GAPDH in RNA was used as the internal control. Total RNA was isolated from heart tissues as described above in Example 2. First-strand cDNA were synthesized by reverse transcriptase and oligo dT. PCR was performed using a LightCycler instrument and the FastStart DNA SYBR Green I Kit (Roche). The PCR reaction mixture contained 2 µL cDNA, 2 µL FastStart DNA Master SYBR® Green I (Roche), 2.4 µL MgCl$_2$ stock solution (25 mM), 0.5 µM of each primer (see Table 1), and sterile H$_2$O in a total volume of 20 µl. All primers were selected using Primer3 software (Whitehead Institute).

TABLE 1

| | Sequence (5' to 3' orientation | SEQ ID NO: |
|---|---|---|
| Human GADPH | | |
| Forward | GAGTCAACGGATTTGGTCGT | 27 |
| Reverse | TTGATTTTGGAGGGATCTCG | 28 |
| Human BNP | | |
| Forward | CTTCTTGCATCTGGCTTTCC | 29 |
| Reverse | AGGGATGTCTGCTCCACCT | 30 |
| Human BNP2 | | |
| Forward | GGACATCGCTTCCTCTTTGTT | 31 |
| Reverse | GAAGGTATTGTGGGCATGGT | 32 |
| Human BNP3 | | |
| Forward | TCCCACAGGTGGTCTGGAAGT | 33 |
| Reverse | TTCTGCACCACTTTGCAGC | 34 |

Products were amplified using 45 cycles of denaturation at 95° C. for 10 sec, annealing at 60° C. for 5 sec, and extension at 72° C. for 10 sec. Purified PCR products from each reaction were measured and served as quantitative standards. All quantitations were normalized to the GAPDH endogenous control. No template controls were used to determine whether fluorescent contaminants were present in the sample. To confirm amplification specificity, the PCR products were subjected to a melting-curve analysis and subsequent agarose gel electrophoresis.

As indicated in Table 2, BNP3 was not found in normal heart tissue. The expression level of BNP-2 in heart failure heart tissue was about 7 times higher than the level in normal heart tissue. Messenger RNA for BNP2 and BNP3 represent up to 5% of all BNP RNA.

TABLE 2

|  | BNP | BNP2 | BNP3 |
|---|---|---|---|
| Normal heart tissue | 58 | 2025 | 0.19 |
| Heart failure heart tissue | 233100 | 13151 | 3807 |

Example 8

Stimulation of cGMP Production with BNP Isoforms

Human umbilical vascular endothelial cells (HUVEC) were cultured in 96-well plates using endothelial cell medium (EGM™-2) supplemented with the components provided by the EGM™-2 BulletKit (CC-3162) (Clonetics, East Rutherford, N.J.). After cells reached about 80% confluency, the plates were washed with phosphate-buffered saline (PBS) then incubated for 30 minutes with 0, 0.1, 1, or 10 µM of synthetic hBNP3 mature peptide (SPKMVQGSGCFGRKM-DRISSSSGLGCKVVQKENQTFPPGFL, SEQ ID NO:35) dissolved in EBM-2 that contained supplements and 0.5 mM IBXM. After incubation, the culture medium was aspirated, and the cells were assayed for intracellular cGMP production using the BIOTRACK cGMP enzyme immunoassay kit (Amersham Pharmacia Biotech). The amount of cGMP was calculated according the standard curve that was generated from parallel reactions within the same experiment. As indicated in Table 3, increasing concentrations of BNP3 resulted in increased production of cGMP.

TABLE 3

|  | Concentration of BNP3 (M) | | | |
|---|---|---|---|---|
|  | 0 | $10^{-10}$ | $10^{-9}$ | $10^{-8}$ |
| cGMP (fmol/well) | 0 | 1 | 18 | 26 |

Example 9

Vasoactivity of BNP Isoforms

Vasoactivity was assessed in an organ chamber using carotid arteries from New Zealand White Rabbits. Following euthanization, carotids were immediately immersed in cold Krebs solution. Arterial rings ~4 mm in length (n=6) were dissected, connected to isometric force displacement transducers, and suspended in organ chambers filled with 25 mL of Krebs (94% $O_2$, 6% $CO_2$). Rings were equilibrated for 1 hour at 37° C. and then incrementally stretched to 3 g. Viability and maximum contraction was determined with 60 mM KCl. After 3 washes with Krebs solution and further equilibration, arteries were pre-contracted with phenylephrine in a titrated fashion to achieve ~80% stable maximal contraction. To study vasoactivity, BNP3 (final conc $10^{-10}$ to $10^{-7}$ M) or vehicle was added to the organ bath in a cumulative manner. Following three further washes and equilibration, the arteries were re-contracted and viability was confirmed by assessment of endothelium independent responses with incremental doses of sodium nitroprusside ($10^{-9}$ to $10^{-5}$ M), an exogenous NO donor.

Vasorelaxation to BNP3 began at $10^{-9}$ M, with vessel responsivity increasing in a dose dependent manner such that ~60% and ~95% complete relaxation was seen at doses of $10^{-8}$M and $10^{-7}$M, respectively. No response was seen in control rings. These data demonstrate that BNP3 is vasoactive at concentrations similar to those reported for other natriuretic peptides. See Best et al., *Cardiovas. Research* 55:375-384 (2002).

Example 10

Intrarenal Infusion of BNP-3 in Normal Dog

To determine the physiological effects of BNP-3, the synthesized peptide was delivered via a direct intrarenal arterial infusion (0.03 ng/kg/min) in normal dogs. Physiologic assessment was performed following a 15 minute run-in period. Infusion of BNP-3 at this dose resulted in elevation of plasma cGMP. This elevation of cGMP was associated with increased urinary flow (6-8 fold) and increased urinary excretion of sodium. Both of these increases normalized during a washout period.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing natriuresis or diuresis in a mammal, comprising administering to said mammal a natriuretic polypeptide comprising:
   (a) a first region comprising residues 1-27 of SEQ ID NO:16, or residues 1-27 of SEQ ID NO:16 with 1 to 5 substitutions, and
   (b) a second region comprising an amino acid sequence having at least 95% sequence identity to the amino acid sequence of SEQ ID NO:1,
wherein said natriuretic polypeptide is administered in an amount effective to increase natriuresis or diuresis in said mammal.

2. The method of claim 1, wherein said first region comprises residues 1-27 of SEQ ID NO:16.

3. The method of claim 1, wherein said first region comprises residues 1-27 of SEQ ID NO:16 with 1 to 5 substitutions.

4. The method of claim 1, wherein said second region comprises the amino acid sequence of SEQ ID NO:1.

5. The method of claim 1, wherein said second region consists of the amino acid sequence of SEQ ID NO:1.

* * * * *

SEQUENCE LISTING

```
<160> NUMBER OF SEQ ID NOS: 38

<210> SEQ ID NO 1
<211> LENGTH: 33
<212> TYPE: PRT
<213> ORGANISM: Homo sapiens

<400> SEQUENCE: 1

Gly Lys His Pro Leu Pro Pro Arg Pro Pro Ser Pro Ile Pro Val Cys
1               5                   10                  15

Asp Thr Val Arg Val Thr Leu Gly Phe Val Val Ser Gly Asn His Thr
            20                  25                  30

Leu
```

<210> SEQ ID NO 2
<211> LENGTH: 14
<212> TYPE: PRT
<213> ORGANISM: Homo sapiens

<400> SEQUENCE: 2

Val Val Gln Lys Glu Asn Gln Thr Phe Pro Pro Gly Phe Leu
1               5                   10

<210> SEQ ID NO 3
<211> LENGTH: 162
<212> TYPE: PRT
<213> ORGANISM: Homo sapiens

<400> SEQUENCE: 3

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
                20                  25                  30

Gly Ser Ala Ser Asp Leu Glu Thr Ser Gly Leu Gln Glu Gln Arg Asn
            35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Ser Gly Leu Gly Cys
        115                 120                 125

Lys Gly Lys His Pro Leu Pro Pro Arg Pro Pro Ser Pro Ile Pro Val
    130                 135                 140

Cys Asp Thr Val Arg Val Thr Leu Gly Phe Val Val Ser Gly Asn His
145                 150                 155                 160

Thr Leu

<210> SEQ ID NO 4
<211> LENGTH: 143
<212> TYPE: PRT
<213> ORGANISM: Homo sapiens

<400> SEQUENCE: 4

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
                20                  25                  30

Gly Ser Ala Ser Asp Leu Glu Thr Ser Gly Leu Gln Glu Gln Arg Asn
            35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys

```
            100                 105                 110
Phe Gly Arg Lys Met Asp Arg Ile Ser Ser Ser Gly Leu Gly Cys
        115                 120                 125

Lys Val Val Gln Lys Glu Asn Gln Thr Phe Pro Pro Gly Phe Leu
        130                 135                 140
```

<210> SEQ ID NO 5
<211> LENGTH: 489
<212> TYPE: DNA
<213> ORGANISM: Homo sapiens

<400> SEQUENCE: 5

```
atggatcccc agacagcacc ttcccgggcg ctcctgctcc tgctcttctt gcatctggct      60
ttcctgggag tcgttccca cccgctgggc agccccggtt cagcctcgga cttggaaacg     120
tccgggttac aggagcagcg caaccatttg cagggcaaac tgtcggagct gcaggtggag     180
cagacatccc tggagcccct ccaggagagc cccgtcccca ggtgtgtctg gaagtcccgg     240
gaggtagcca ccgagggcat ccgtgggcac cgcaaaatgg tcctctacac cctgcgggca     300
ccacgaagcc ccaagatggt gcaagggtct ggctgctttg ggaggaagat ggaccggatc     360
agctcctcca gtggcctggg ctgcaaaggt aagcaccccc tgccaccccg gccgccttcc     420
cccattccag tgtgtgacac tgttagagtc actttggggt tgttgtctc tgggaaccac     480
actctttga                                                            489
```

<210> SEQ ID NO 6
<211> LENGTH: 432
<212> TYPE: DNA
<213> ORGANISM: Homo sapiens

<400> SEQUENCE: 6

```
atggatcccc agacagcacc ttcccgggcg ctcctgctcc tgctcttctt gcatctggct      60
ttcctgggag tcgttccca cccgctgggc agccccggtt cagcctcgga cttggaaacg     120
tccgggttac aggagcagcg caaccatttg cagggcaaac tgtcggagct gcaggtggag     180
cagacatccc tggagcccct ccaggagagc cccgtcccca ggtgtgtctg gaagtcccgg     240
gaggtagcca ccgagggcat ccgtgggcac cgcaaaatgg tcctctacac cctgcgggca     300
ccacgaagcc ccaagatggt gcaagggtct ggctgctttg ggaggaagat ggaccggatc     360
agctcctcca gtggcctggg ctgcaaagtg gtgcagaaag agaaccaaac atttcctcct     420
ggtttcctct aa                                                        432
```

<210> SEQ ID NO 7
<211> LENGTH: 44
<212> TYPE: PRT
<213> ORGANISM: Pongo pygmaeus

<400> SEQUENCE: 7

```
Gly Glu His Pro Leu Pro Pro Arg Leu Pro Ala Pro Ile Pro Val Cys
  1               5                  10                  15

Asp Thr Val Arg Val Thr Leu Gly Phe Val Val Ser Gly Asn His Thr
                 20                  25                  30

Leu Arg Lys Cys His Leu Asp Ile Thr Ser Ser Cys
            35                  40
```

<210> SEQ ID NO 8
<211> LENGTH: 58
<212> TYPE: PRT

<213> ORGANISM: Sus scrofa

<400> SEQUENCE: 8

Gly Glu His Pro Pro Pro Phe Pro Leu His Ala Pro Val Ser Ile Thr
1               5                   10                  15

Ser Gly Phe Asp Val Ser Gly Asp Gln Thr Pro Arg Lys Gly His Leu
            20                  25                  30

Asp Ile Thr Leu Ser Cys Cys Gln Ser Ser Arg Pro Arg Ser Ala Phe
        35                  40                  45

Leu Glu Lys Leu Asn Leu Asp Ser Ile His
    50                  55

<210> SEQ ID NO 9
<211> LENGTH: 33
<212> TYPE: PRT
<213> ORGANISM: Pan troglodytes

<400> SEQUENCE: 9

Gly Glu His Pro Leu Pro Pro Arg Pro Pro Ser Pro Ile Pro Val Cys
1               5                   10                  15

Asp Thr Val Arg Val Thr Leu Gly Phe Val Val Ser Gly Asn His Thr
            20                  25                  30

Leu

<210> SEQ ID NO 10
<211> LENGTH: 78
<212> TYPE: PRT
<213> ORGANISM: Ovis aries

<400> SEQUENCE: 10

Gly Glu Arg Leu Ser Ala Phe Pro Leu His Ile Thr Ile Arg Ala Thr
1               5                   10                  15

Ser Gly Ser Asp Val Ser Gly Asp Gln Ile Leu Asn Lys Glu His His
            20                  25                  30

Ser Ser Leu Leu Ala Val Leu Arg Ala Lys Ala Cys Leu Ser Gly Asn
        35                  40                  45

Ile Lys Phe Gly Gln His Ser Leu Ser Cys Leu Gly Ala Pro Ser Ile
    50                  55                  60

His Leu Leu Pro Leu Thr Glu Arg Gly Arg Ile Phe Arg Met
65                  70                  75

<210> SEQ ID NO 11
<211> LENGTH: 26
<212> TYPE: PRT
<213> ORGANISM: Mus musculus

<400> SEQUENCE: 11

Gly Glu His Leu Pro Cys His Phe Pro Ala Lys Leu His Thr His Pro
1               5                   10                  15

Ile Pro Val His Ala Thr Leu Arg Gly Pro
            20                  25

<210> SEQ ID NO 12
<211> LENGTH: 33
<212> TYPE: PRT
<213> ORGANISM: Gorilla gorilla

<400> SEQUENCE: 12

Gly Glu His Pro Leu Pro Pro Arg Pro Pro Ser Pro Ile Pro Val Cys
1               5                   10                  15

```
Asp Thr Val Arg Val Thr Leu Gly Phe Val Val Ser Gly Asn His Thr
                20                  25                  30

Leu

<210> SEQ ID NO 13
<211> LENGTH: 86
<212> TYPE: PRT
<213> ORGANISM: Felis catus

<400> SEQUENCE: 13

Gly Lys Pro Pro Cys Gln Leu Asp Pro Ala Pro Leu Leu Trp
 1               5                  10                  15

Val Pro Pro Ser Glu Pro Leu Leu Gly Leu Leu Ser Leu Gly Thr Asn
                20                  25                  30

Ser Glu Lys Lys Thr Leu Gly Leu Tyr Ser Leu Leu Thr Val Leu
                35                  40                  45

Lys Ala Lys Gly Arg Leu Ser Gly Asn Ile Lys Cys Gly His His Ser
 50                  55                  60

Leu Leu Cys Pro Pro Arg Val Thr His Leu Leu Leu Pro Leu Trp Pro
65                   70                  75                  80

Lys Gly Ala Glu Ser Pro
                85

<210> SEQ ID NO 14
<211> LENGTH: 169
<212> TYPE: PRT
<213> ORGANISM: Canis familiaris

<400> SEQUENCE: 14

Met Glu Pro Cys Ala Ala Leu Pro Arg Ala Leu Leu Leu Leu Leu Phe
 1               5                  10                  15

Leu His Leu Ser Pro Leu Gly Gly Arg Pro His Pro Leu Gly Gly Arg
                20                  25                  30

Ser Pro Thr Ser Glu Ala Ser Glu Ala Ser Glu Ala Ser Gly Leu Trp
                35                  40                  45

Ala Val Gln Glu Leu Leu Gly Arg Leu Lys Asp Ala Val Ser Glu Leu
 50                  55                  60

Gln Ala Glu Gln Leu Ala Leu Glu Pro Leu His Arg Ser His Ser Pro
65                   70                  75                  80

Ala Glu Ala Pro Glu Ala Gly Glu Glu Arg Pro Val Gly Val Leu Ala
                85                  90                  95

Pro His Asp Ser Val Leu Gln Ala Leu Arg Arg Leu Arg Ser Pro Lys
                100                 105                 110

Met Met His Lys Ser Gly Cys Phe Gly Arg Arg Leu Asp Arg Ile Gly
                115                 120                 125

Ser Leu Ser Gly Leu Gly Cys Asn Gly Lys Pro Pro Pro Cys His Leu
 130                 135                 140

Gly Ser Pro Ser Pro Ala Pro Trp Val Arg Pro Leu Glu Pro Leu Leu
145                 150                 155                 160

Gly Leu Leu Ser Arg Gly Ile Thr Leu
                165

<210> SEQ ID NO 15
<211> LENGTH: 15
<212> TYPE: PRT
<213> ORGANISM: Dendroaspis angusticeps
```

```
<400> SEQUENCE: 15

Pro Ser Leu Arg Asp Pro Arg Pro Asn Ala Pro Ser Thr Ser Ala
 1               5                  10                  15

<210> SEQ ID NO 16
<211> LENGTH: 32
<212> TYPE: PRT
<213> ORGANISM: Homo sapiens

<400> SEQUENCE: 16

Ser Pro Lys Met Val Gln Gly Ser Gly Cys Phe Gly Arg Lys Met Asp
 1               5                  10                  15

Arg Ile Ser Ser Ser Ser Gly Leu Gly Cys Lys Val Leu Arg Arg His
            20                  25                  30

<210> SEQ ID NO 17
<211> LENGTH: 41
<212> TYPE: PRT
<213> ORGANISM: Dendroaspis angusticeps

<400> SEQUENCE: 17

Glu Val Lys Tyr Asp Pro Cys Phe Gly His Lys Ile Asp Arg Ile Asn
 1               5                  10                  15

His Val Ser Asn Leu Gly Cys Pro Ser Leu Arg Asp Pro Arg Pro Asn
            20                  25                  30

Ala Pro Ser Thr Ser Ala Asp Asn Pro
            35                  40

<210> SEQ ID NO 18
<211> LENGTH: 28
<212> TYPE: PRT
<213> ORGANISM: Homo sapiens

<400> SEQUENCE: 18

Ser Leu Arg Arg Ser Ser Cys Phe Gly Gly Arg Met Asp Arg Ile Gly
 1               5                  10                  15

Ala Gln Ser Gly Leu Gly Cys Asn Ser Phe Arg Tyr
            20                  25

<210> SEQ ID NO 19
<211> LENGTH: 22
<212> TYPE: PRT
<213> ORGANISM: Homo sapiens

<400> SEQUENCE: 19

Gly Leu Ser Lys Gly Cys Phe Gly Leu Lys Leu Asp Arg Ile Gly Ser
 1               5                  10                  15

Met Ser Gly Leu Gly Cys
            20

<210> SEQ ID NO 20
<211> LENGTH: 34
<212> TYPE: PRT
<213> ORGANISM: Artificial Sequence
<220> FEATURE:
<223> OTHER INFORMATION: exemplary motif
<221> NAME/KEY: VARIANT
<222> LOCATION: 2
<223> OTHER INFORMATION: Xaa = Glu or Lys
<221> NAME/KEY: VARIANT
<222> LOCATION: 3
<223> OTHER INFORMATION: Xaa = Pro, His, or Arg
<221> NAME/KEY: VARIANT
<222> LOCATION: 4
```

```
<223> OTHER INFORMATION: Xaa = Pro or Leu
<221> NAME/KEY: VARIANT
<222> LOCATION: 5
<223> OTHER INFORMATION: Xaa = Pro, Leu, or Ser
<221> NAME/KEY: VARIANT
<222> LOCATION: 6
<223> OTHER INFORMATION: Xaa = Cys or Pro
<221> NAME/KEY: VARIANT
<222> LOCATION: 7
<223> OTHER INFORMATION: Xaa = Pro, His, Gln, or Arg
<221> NAME/KEY: VARIANT
<222> LOCATION: 8
<223> OTHER INFORMATION: Xaa = Arg, Phe, or Leu
<221> NAME/KEY: VARIANT
<222> LOCATION: 9
<223> OTHER INFORMATION: Xaa = Asp, Gly, or absent
<221> NAME/KEY: VARIANT
<222> LOCATION: 10
<223> OTHER INFORMATION: Xaa = Ser, Pro, or Leu
<221> NAME/KEY: VARIANT
<222> LOCATION: 11
<223> OTHER INFORMATION: Xaa = Pro or absent
<221> NAME/KEY: VARIANT
<222> LOCATION: 12
<223> OTHER INFORMATION: Xaa = Ser, Ala, or absent
<221> NAME/KEY: VARIANT
<222> LOCATION: 13
<223> OTHER INFORMATION: Xaa = Pro or Ala
<221> NAME/KEY: VARIANT
<222> LOCATION: 14
<223> OTHER INFORMATION: Xaa = Ala, Phe, Ile, or Leu
<221> NAME/KEY: VARIANT
<222> LOCATION: 15
<223> OTHER INFORMATION: Xaa = Pro, Lys, or Leu
<221> NAME/KEY: VARIANT
<222> LOCATION: 16
<223> OTHER INFORMATION: Xaa = Val, Leu, or Trp
<221> NAME/KEY: VARIANT
<222> LOCATION: 17
<223> OTHER INFORMATION: Xaa = Cys, His, or Val
<221> NAME/KEY: VARIANT
<222> LOCATION: 18
<223> OTHER INFORMATION: Xaa = Asp, Ala, Ile, Thr, Pro, or Arg
<221> NAME/KEY: VARIANT
<222> LOCATION: 19
<223> OTHER INFORMATION: Xaa = Thr, Pro, or His
<221> NAME/KEY: VARIANT
<222> LOCATION: 20
<223> OTHER INFORMATION: Xaa = Val, Ile, Pro, Val, Ser, or Leu
<221> NAME/KEY: VARIANT
<222> LOCATION: 21
<223> OTHER INFORMATION: Xaa = Arg, Ser, Ile, or Glu
<221> NAME/KEY: VARIANT
<222> LOCATION: 22
<223> OTHER INFORMATION: Xaa = Val, Ile, Ala, or Pro
<221> NAME/KEY: VARIANT
<222> LOCATION: 23
<223> OTHER INFORMATION: Xaa = Thr, Val, or Leu
<221> NAME/KEY: VARIANT
<222> LOCATION: 24
<223> OTHER INFORMATION: Xaa = Leu, Ser, or His
<221> NAME/KEY: VARIANT
<222> LOCATION: 25
<223> OTHER INFORMATION: Xaa = Gly or Ala
<221> NAME/KEY: VARIANT
<222> LOCATION: 26
<223> OTHER INFORMATION: Xaa = Phe, Ser, Thr, or Leu
<221> NAME/KEY: VARIANT
<222> LOCATION: 27
<223> OTHER INFORMATION: Xaa = Val, Asp, or Leu
<221> NAME/KEY: VARIANT
<222> LOCATION: 28
<223> OTHER INFORMATION: Xaa = Val, Leu, or Ser
<221> NAME/KEY: VARIANT
<222> LOCATION: 29
<223> OTHER INFORMATION: Xaa = Ser, Arg, or Leu
<221> NAME/KEY: VARIANT
<222> LOCATION: 31
<223> OTHER INFORMATION: Xaa = Asn, Asp, Pro, or Thr
```

```
<221> NAME/KEY: VARIANT
<222> LOCATION: 32
<223> OTHER INFORMATION: Xaa = His, Gln, Asn, or Thr
<221> NAME/KEY: VARIANT
<222> LOCATION: 33
<223> OTHER INFORMATION: Xaa = Thr, Ile, or Ser
<221> NAME/KEY: VARIANT
<222> LOCATION: 34
<223> OTHER INFORMATION: Xaa = Pro, Leu, or Glu

<400> SEQUENCE: 20

Gly Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Gly Xaa Xaa
            20                  25                  30

Xaa Xaa

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
agacatggat ccccagacag                                               20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
caagaggaag cgatgtccag                                               20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
ttctctccag cgacatggag                                               20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
ggactctttc tgctccaagg                                               20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
agacatggat ccccagacag                                               20
```

-continued

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
tttctgcacc actttgcagc                                               20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
gagtcaacgg atttggtcgt                                               20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
ttgattttgg agggatctcg                                               20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
cttcttgcat ctggcttttcc                                              20

<210> SEQ ID NO 30
<211> LENGTH: 19
<212> TYPE: DNA
<213> ORGANISM: Artificial Sequence
<220> FEATURE:
<223> OTHER INFORMATION: Primer

<400> SEQUENCE: 30
agggatgtct gctccacct                                                19

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
ggacatcgct tcctctttgt t                                             21

<210> SEQ ID NO 32
<211> LENGTH: 20
<212> TYPE: DNA
<213> ORGANISM: Artificial Sequence
<220> FEATURE:

<223> OTHER INFORMATION: Primer

<400> SEQUENCE: 32
gaaggtattg tgggcatggt                                           20

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
tcccacaggt ggtctggaag t                                         21

<210> SEQ ID NO 34
<211> LENGTH: 19
<212> TYPE: DNA
<213> ORGANISM: Artificial Sequence
<220> FEATURE:
<223> OTHER INFORMATION: Primer

<400> SEQUENCE: 34
ttctgcacca ctttgcagc                                            19

<210> SEQ ID NO 35
<211> LENGTH: 41
<212> TYPE: PRT
<213> ORGANISM: Homo sapiens

<400> SEQUENCE: 35

Ser Pro Lys Met Val Gln Gly Ser Gly Cys Phe Gly Arg Lys Met Asp
 1               5                  10                  15

Arg Ile Ser Ser Ser Ser Gly Leu Gly Cys Lys Val Val Gln Lys Glu
            20                  25                  30

Asn Gln Thr Phe Pro Pro Gly Phe Leu
        35                  40

<210> SEQ ID NO 36
<211> LENGTH: 60
<212> TYPE: PRT
<213> ORGANISM: Homo sapiens

<400> SEQUENCE: 36

Ser Pro Lys Met Val Gln Gly Ser Gly Cys Phe Gly Arg Lys Met Asp
 1               5                  10                  15

Arg Ile Ser Ser Ser Ser Gly Leu Gly Cys Lys Gly Lys His Pro Leu
            20                  25                  30

Pro Pro Arg Pro Pro Ser Pro Ile Pro Val Cys Asp Thr Val Arg Val
        35                  40                  45

Thr Leu Gly Phe Val Val Ser Gly Asn His Thr Leu
    50                  55                  60

<210> SEQ ID NO 37
<211> LENGTH: 32
<212> TYPE: PRT
<213> ORGANISM: Canis familiaris

<400> SEQUENCE: 37

Gly Lys Pro Pro Pro Cys Arg Leu Gly Ser Pro Ser Pro Ala Pro Trp
 1               5                  10                  15

Val Arg Pro Leu Glu Pro Leu Leu Gly Leu Leu Ser Arg Gly Ile Thr

-continued

```
<210> SEQ ID NO 38
<211> LENGTH: 510
<212> TYPE: DNA
<213> ORGANISM: Canis familiaris

<400> SEQUENCE: 38
atggagccct gcgcagcgct gccccgggcc ctcctgctcc tcctgttctt gcacctgtcg      60
ccactcggag gccgccccca cccgctgggc ggccgcagcc ccacctcgga agcctcggaa     120
gcctcggaag cctcggggtt gtgggccgtg caggagctgc tgggccgtct gaaggacgca     180
gtttcagagc tgcaggcaga gcagttggcc ctggaacccc tgcaccggag ccacagcccc     240
gcagaagccc cggaggccgg ggaggaacgc cccgtggggg tccttgcacc ccatgacagt     300
gtcctccagg ccctgagaag actacgcagc cccaagatga tgcacaagtc agggtgcttt     360
ggccggaggc tggaccggat cggctccctc agtggcctgg gctgcaatgg taagccgcct     420
ccctgccacc ttggctcccc ctccccagcc ccctgggttc gacccttgga accccttctg     480
ggtttgttgt ctcgggggat cacactctga                                      510
```